US008118819B2

(12) United States Patent
Miyamoto et al.

(10) Patent No.: US 8,118,819 B2
(45) Date of Patent: Feb. 21, 2012

(54) MEDICAL TREATMENT TOOL

(75) Inventors: Satoshi Miyamoto, Tokyo (JP); Norio Onishi, Tokyo (JP)

(73) Assignee: Olympus Corporation (JP)

(*) Notice: Subject to any disclaimer, the term of this patent is extended or adjusted under 35 U.S.C. 154(b) by 544 days.

(21) Appl. No.: 11/399,538

(22) Filed: Apr. 6, 2006

(65) Prior Publication Data

US 2006/0259043 A1    Nov. 16, 2006

Related U.S. Application Data

(63) Continuation of application No. PCT/JP2004/015004, filed on Oct. 5, 2004.

(30) Foreign Application Priority Data

Oct. 8, 2003  (JP) ................................ 2003-349572

(51) Int. Cl.
    *A61B 17/10*    (2006.01)
(52) U.S. Cl. ........................................ 606/139
(58) Field of Classification Search ............... 606/139
    See application file for complete search history.

(56) References Cited

U.S. PATENT DOCUMENTS

| 3,829,975 | A | * | 8/1974 | Balson | 433/39 |
| 4,018,229 | A | * | 4/1977 | Komiya | 606/139 |
| 5,540,709 | A | * | 7/1996 | Ramel | 606/183 |
| 5,542,843 | A | * | 8/1996 | Price | 433/4 |
| 5,782,864 | A | * | 7/1998 | Lizardi | 606/232 |
| 5,855,586 | A | * | 1/1999 | Habara et al. | 606/144 |
| 6,051,003 | A | * | 4/2000 | Chu et al. | 606/140 |
| 2002/0133170 | A1 | * | 9/2002 | Tsuruta | 606/127 |
| 2003/0144673 | A1 | * | 7/2003 | Onuki et al. | 606/139 |

FOREIGN PATENT DOCUMENTS

| EP | 0 591 991 A2 | 10/1993 |
| JP | S48-71090 | 9/1973 |
| JP | S54-30692 | 3/1979 |
| JP | 2001-440 | 1/2001 |
| JP | 2003-19139 | 1/2003 |
| JP | 2003-204966 | 7/2003 |

OTHER PUBLICATIONS

Search Report issued by European Patent Office in connection with corresponding application No. EP 04 79 2251 on Nov. 30, 2010.

* cited by examiner

*Primary Examiner* — Ryan Severson
*Assistant Examiner* — Julie A Szpira
(74) *Attorney, Agent, or Firm* — Ostrolenk Faber LLP

(57) ABSTRACT

A medical treatment tool comprises: a flexible wire; a first wire holding member which holds the wire; a second wire holding member capable of holding the wire between itself and the first wire holding member; a first sheath which is provided in contact with a proximal side of the second wire holding member; a second sheath which is provided in a back-and-forth movable manner with respect to the first sheath; and a sheath operation portion which operates the second sheath. The first wire holding member and the second sheath have a connection device for connecting them to each other; the first wire holding member and the second wire holding member have a latching device which latches them to each other when holding the wire there between, and a cutting device which cuts the wire; and the second wire holding member has a connection releasing device which releases the connection of the connection device, when latched by the first wire holding member.

9 Claims, 30 Drawing Sheets

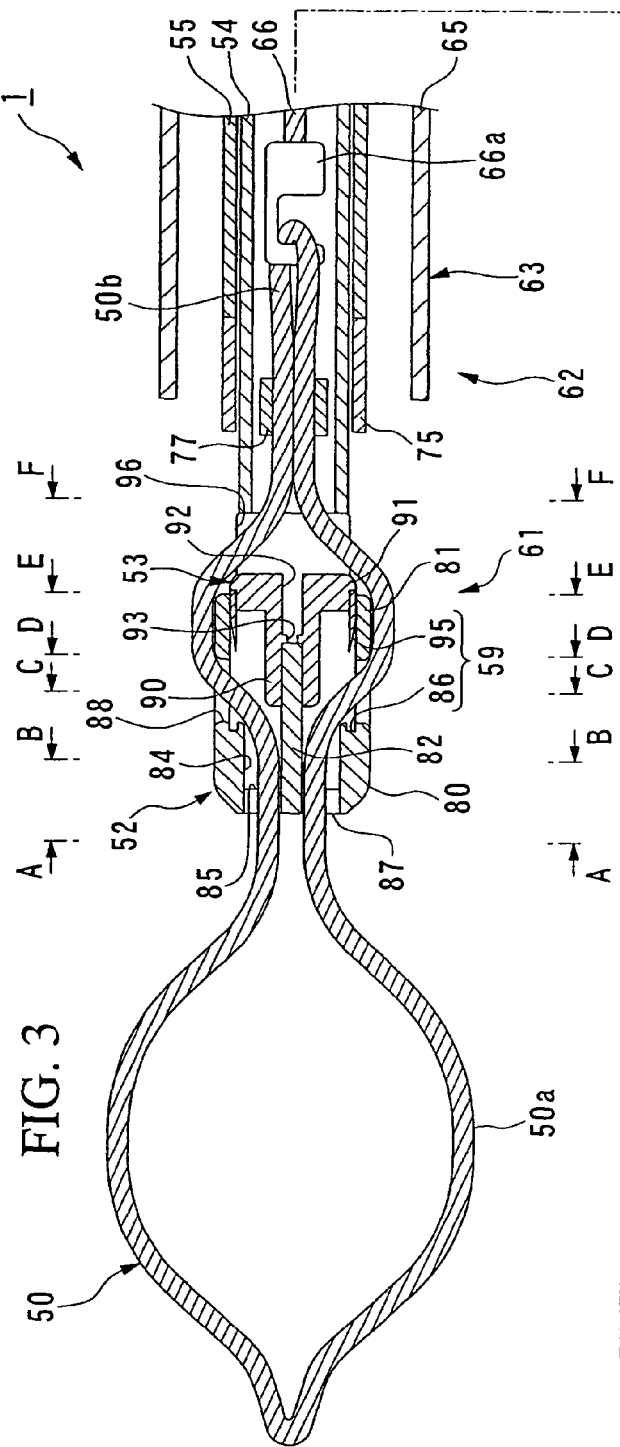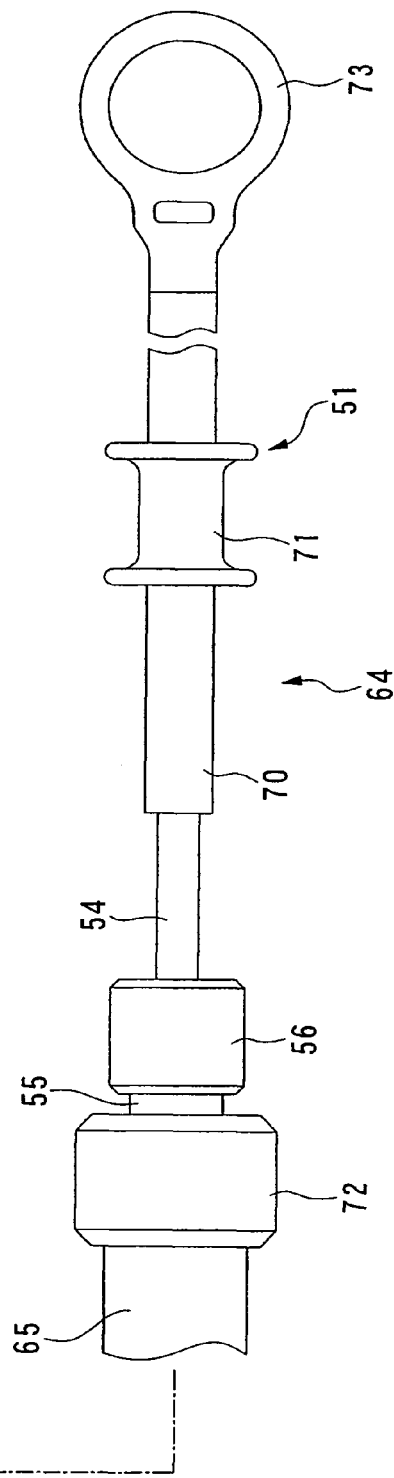
FIG. 3

MEDICAL TREATMENT TOOL

CROSS REFERENCE TO RELATED APPLICATION

The is a continuation application of PCT/JP2004/015004 filed Oct. 5, 2004, which claim priority to Japanese Patent Application 2003-349572 filed Oct. 8, 2003, which is hereby incorporated by reference. The PCT International Application was published in the Japanese language.

TECHNICAL FIELD

The present invention relates to a medical treatment tool which is inserted into a body cavity, so as to perform a predetermined treatment such as ligation and suture, on a biological tissue.

BACKGROUND ART

Currently, various tools are proposed for a medical treatment tool which is inserted into a body cavity by inserting through a treatment tool channel of an endoscope, so as to perform a predetermined treatment such as ligation and suture on a biological tissue, and obtain a biological sample. As a medical treatment tool of this kind, for example as disclosed in Japanese Unexamined Patent Application, First Publication No. 2003-204966 (paragraph Nos. 0046 to 0061, FIGS. 9 to 14), there is known a medical ligation unit capable of ligating an affected part in the body cavity by a ligation wire, and cutting the ligation wire that performs the ligation, by a series of operations.

This medical ligation unit comprises a medical ligation tool which is anchored in the living body, and an operating device which performs a ligation operation by guiding the medical ligation tool into the body. The medical ligation tool has the aforementioned ligation wire which has a folded portion on the proximal side, and a fixing member which fixes the ligation wire in a back-and-forth movable manner, ahead of the folded portion. The fixing member comprises a first member and a second member.

The first member is formed in a cylindrical shape, and has a press-fit portion provided on the distal side, and a large diameter portion having annular cutting blades provided on the proximal side. On the peripheral face of this large diameter portion is formed coupling catches. Moreover, the second member has; a fixing hollow which is arranged so as to be movable back-and-forth in the distal side of the first member formed in a cylindrical shape, and into which the press-fit portion is press-fitted, and coupling holes provided in the periphery of the cylindrical portion, and capable of coupling with the coupling catches.

Moreover, the ligation wire is passed from the distal end of the second member, through the fixing hollow, and comes out from the side holes of the cylindrical portion to the outside, and is then guided from the wire guide provided on the proximal side of the large diameter portion of the first member to the inside, so as to become the folded portion.

The operating device has an inner sheath which is in contact with the proximal side of the second member. The proximal side of the inner sheath is connected with an operation portion main body having a finger catch ring. Moreover, the operation portion main body is attached with a slider which is back-and-forth movable with respect to the operation portion main body. The slider is connected with an operation wire, which is inserted through the inner sheath, and has a coupling member on the distal end. This coupling member is designed to be coupled with the folded portion of the ligation wire. That is, by operating the slider back-and forth while the operation portion main body is fixed, the diameter of the ligation wire can be expanded or reduced.

In the case where an affected part in a body cavity is ligated by the medical ligation unit constituted in such a manner, the medical ligation unit is inserted into the body cavity via an endoscope device or the like, and the ligation wire is hooked on the affected part.

In this condition, the operation portion main body is fixed, and the slider is moved in the proximal direction, so as to move the operation wire backward. As a result, the ligation wire is pulled into the second member, and hence the diameter of the ligation wire is reduced. By so doing, the affected part is tightly bound, and the blood flow can be stopped. Moreover, since the affected part is pulled to the second member side by further pulling the operation wire, the second member is pushed to the first member side via the affected part. By the movement of the second member, the press-fit portion of the first member is relatively moved into the fixing hollow. Consequently, the ligation wire in the fixing hollow is held and fixed between the inner face of the fixing hollow and the outer face of the press-fit portion. Moreover, the ligation wire is cut by the cutting blades of the first member, on the clamped proximal side. Furthermore, at this time, the coupling catches are engaged into the coupling holes, so that the first member and the second member are mutually coupled.

As described above, after the affected part is tightly bound, the second member is moved toward the first member via the affected part, so as to couple both members. At the same time, the ligation wire is held and fixed between both members, and the ligation wire is cut rearward of the holding position, thus completing the ligation treatment.

The present invention takes the above problems into consideration with an object of providing a medical treatment tool capable of fixing and cutting a wire such as a ligation wire, without involving the biological tissue, after a predetermined treatment on the biological tissue.

DISCLOSURE OF INVENTION

In order to achieve the above object, the present invention provides the following means.

A first aspect of the present invention provides a medical treatment tool, comprising: a flexible wire which performs a predetermined treatment on a biological tissue; a wire operation portion which operates the wire back-and-forth; a first wire holding member which is provided in a back-and-forth movable manner with respect to the wire, to hold the wire; a second wire holding member which is provided on a proximal side of the first wire holding member, in a back-and-forth movable manner in an axial direction, and is capable of holding the wire between itself and the first wire holding member; a flexible first sheath which is provided in contact with a proximal side of the second wire holding member; a flexible second sheath which is provided to cover the first sheath, in a back-and-forth movable manner with respect to the first sheath; and a sheath operation portion which operates the second sheath back-and-forth; wherein the first wire holding member and the second sheath have a connection device which connects them to each other; the first wire holding member and the second wire holding member have a latching device which latches them to each other when holding the wire therebetween, and a cutting device which cuts the wire at a proximal side from the holding position; and the second wire holding member has a connection releasing device which releases the connection of the connection device, when latched by the first wire holding member.

In the medical treatment tool according to the first aspect of the present invention, after completion of a predetermined treatment on a biological tissue by means of the wire, by operating the wire back-and-forth by the wire operation portion, the sheath operation portion is moved in the proximal direction, so as to move the second sheath backward with respect to the first sheath. As a result the first wire holding member connected by the connection device is moved in the proximal direction, that is, toward the second wire holding member. In this case, since the second wire holding member is in contact with the distal end of the first sheath, it is not moved in the proximal direction. That is, the first wire holding member and the second wire holding member reliably come closer. Moreover, by a further operation of the sheath operation portion, both members are made closer to each other so as to hold the wire therebetween. Furthermore, in this case, both members can be mutually latched while the wire is held therebetween by means of the latching device, and the wire can be cut on the proximal side from the holding position, by the cutting device.

Furthermore, when both members are latched, the connection releasing device releases the connection of the connection device, and hence the first wire holding member and the second sheath are detached. Therefore, if the second sheath is operated backward via the sheath operation portion, the first member and the second member that have been mutually latched while the wire is held, fixed, and cut, can be detached from the second sheath.

In this manner, the first wire holding member is moved toward the second wire holding member without involving the biological tissue, so that the wire which has completed a predetermined treatment, can be held and fixed between both members, and can be cut rearward of the holding position. Consequently, since the wire can be reliably held, fixed, and cut, regardless of the condition of the biological tissue, the operability and the accuracy of the workability can be improved. Moreover, since by a series of operations of the sheath operation portion at approximately the same time, the wire can be held, fixed, and cut, by latching the first wire holding member and the second wire holding member, and the connection of the first wire holding member and the second sheath can be released, effective operation can be performed.

A second aspect of the present invention provides a medical treatment tool of the first aspect of the present invention, wherein the cutting device cuts the wire inside of the first wire holding member.

In the medical treatment tool according this aspect of the present invention, since when cutting the wire, the cutting device cuts the wire inside of the first wire holding member, the cut ends of the cut wire are not exposed to the outside of the first wire holding member. Consequently, interference with other treatment tools in the body can be prevented.

A third aspect of the present invention provides a medical treatment tool, comprising: a flexible wire which performs a predetermined treatment on a biological tissue; a wire operation portion which operates the wire back-and-forth; a first wire holding member which is provided in a back-and-forth movable manner with respect to the wire, to hold the wire; a second wire holding member which is provided on a proximal side of the first wire holding member, in a back-and-forth movable manner in an axial direction, and which holds the wire between itself and the first wire holding member; a flexible first sheath which is provided in contact with a proximal side of the second wire holding member; a flexible second sheath which is provided to cover the first sheath, in a back-and-forth movable manner with respect to the first sheath; a cutting member which is provided on a distal end of the second sheath, and has a cutting blade which cuts the wire at a proximal side from the holding position, arranged on a distal side from the wire; and a sheath operation portion which operates the second sheath back-and-forth; wherein the first wire holding member and the second sheath have a connection device which connects them to each other; the first wire holding member and the second wire holding member have a latching device which latches them to each other when holding the wire therebetween; and the second wire holding member has a connection releasing device which releases the connection of the connection device, when latched by the first wire holding member.

In the medical treatment tool according to this aspect of the present invention, after completion of a predetermined treatment on a biological tissue by means of the wire, by operating the wire back-and-forth by the wire operation portion, the sheath operation portion is moved in the proximal direction, so as to move the second sheath backward with respect to the first sheath. As a result the first wire holding member connected by the connection device is moved in the proximal direction, that is, toward the second wire holding member. In this case, since the second wire holding member is in contact with the distal end of the first sheath, it is not moved in the proximal direction. That is, the first wire holding member and the second wire holding member reliably come closer. Furthermore, the cutting blade provided on the distal end of the second sheath is also moved to the second wire holding member side, together with the first wire holding member. Moreover, by a further operation of the sheath operation portion, both wire holding members are made closer to each other so as to hold the wire therebetween. Furthermore, in this case, both wire holding members can be mutually latched while the wire is held therebetween, by means of the latching device. At this time, since the relative position between the cutting blade and the first wire holding member is not changed, the wire is not cut by the cutting blade.

Furthermore, when both wire holding members are latched, the connection releasing device releases the connection of the connection device, and hence the first wire holding member and the second sheath are detached. As a result, by further operating the sheath operation portion backward, the cutting blade is moved in the proximal direction, to cut the wire on the proximal side from the holding position.

In this manner, the first wire holding member is moved toward the second wire holding member without involving the biological tissue, so that the wire which has completed a predetermined treatment, can be held and fixed between both wire holding members, and can be cut rearward of the holding position. Consequently, since the wire can be reliably held, fixed, and cut, regardless of the condition of the biological tissue, the operability and the accuracy of the workability can be improved.

Moreover, since by a series of operations of the sheath operation portion at approximately the same time, the wire can be held and fixed by latching the first wire holding member and the second wire holding member, the connection of the first wire holding member and the second sheath can be released, and the wire can be cut by the connection release, effective operation can be performed. In particular, since the wire can be cut after the wire is held and fixed, both operations can be respectively and reliably performed. Consequently, the reliability of work can be improved.

A fourth aspect of the present invention provides a medical treatment tool of the third aspect of the present invention, wherein the second wire holding member has a wire storage portion which contains a cut end of the wire after cutting, thereinside.

In the medical treatment tool according this aspect of the present invention, since the second wire holding member contains the cut ends of the cut wire, in the wire storage portion, the cut ends are not exposed to the outside of the second wire holding member. Consequently, interference with other treatment tools in the body can be prevented.

A fifth aspect of the present invention provides a medical treatment tool of the third or fourth aspect of the present invention, wherein the cutting member is detachably provided on the second sheath.

In the medical treatment tool according this aspect of the present invention, the cutting member can be detached from the second sheath and exchanged. Consequently, the cutting blade can be always kept in a new condition, and its sharpness can be maintained.

A sixth aspect of the present invention provides a medical treatment tool of the first or third aspect of the present invention, wherein: the connection device comprises a projection which is projected from the second sheath in a distal direction, and has a catch projected toward the inside of the second sheath, on the distal end, and a latch hole which is provided in the periphery of the first connection member, and is capable of latching with the catch; and the connection releasing device is a coupling catch which is engaged into the latch hole in the latched condition, and is capable of pushing out the catch from the latch hole.

In the medical treatment tool according this aspect of the present invention, the catch of the projection is engaged in the latch hole and latched, so that the first wire holding member and the second sheath are mutually connected. Moreover, when the wire is held between the first wire holding member and the second wire holding member, the coupling catch of the second connection member is engaged in the latch hole, and pushes out the catch from the inside of the latch hole. As a result, the connection between the first wire holding member and the second sheath can be reliably released.

A seventh aspect of the present invention provides a medical treatment tool of the sixth aspect of the present invention, wherein the latching device comprises the latch hole and the coupling catch.

In the medical treatment tool according this aspect of the present invention, when the first wire holding member and the second wire holding member hold the wire therebetween, the coupling catch is engaged in the latch hole, so that both members can be latched. By using the latch hole of the connection device and the coupling catch serving as the connection releasing device in this manner, both members can be reliably latched, and hence it is not necessary to provide the latching device separately. Consequently, the structure can be simplified.

An eighth aspect of the present invention provides a medical treatment tool of the first or third aspect of the present invention, wherein the wire is a ligation wire which ligates a biological tissue.

In the medical treatment tool according this aspect of the present invention, after the ligation wire is hooked on the biological tissue in the body, the wire operation portion is operated in the proximal direction, so that the biological tissue can be ligated. Then, after the ligation, the ligation wire can be reliably held and fixed between the first wire holding member and the second wire holding member and then cut, regardless of the condition of the biological tissue.

A ninth aspect of the present invention provides a medical treatment tool of the first or third aspect of the present invention, wherein the wire is a suture thread for suturing a biological tissue, and there is provided: a drop-off preventing member connected to a distal end of the suture thread; and a suture needle main body which detachably contains the drop-off preventing member, and has a needle portion for piercing a biological tissue, on a distal end.

In the medical treatment tool according this aspect of the present invention, while the biological tissue in the body is being pierced with the needle portion, the suture needle main body is operated so as to suture the biological tissue. After the suture, by detaching the drop-off preventing member from the suture needle main body, and by operating the wire operation portion in the proximal direction, the biological tissue is gathered between the drop-off preventing member and the first wire holding member. Moreover, in this condition, the suture thread can be reliably held and fixed between the first wire holding member and the second wire holding member and then cut, regardless of the condition of the biological tissue.

BRIEF DESCRIPTION OF THE DRAWINGS

FIG. 3 is a block diagram of the medical treatment tool of the present embodiment shown in FIG. 1.

BEST MODE FOR CARRYING OUT THE INVENTION

A first embodiment of a medical treatment tool according to the present invention is described with reference to FIG. 1 to FIG. 18. However, the present invention is not limited to the respective embodiments below, and for example, the components of these embodiments may be suitably combined.

Figure 1:
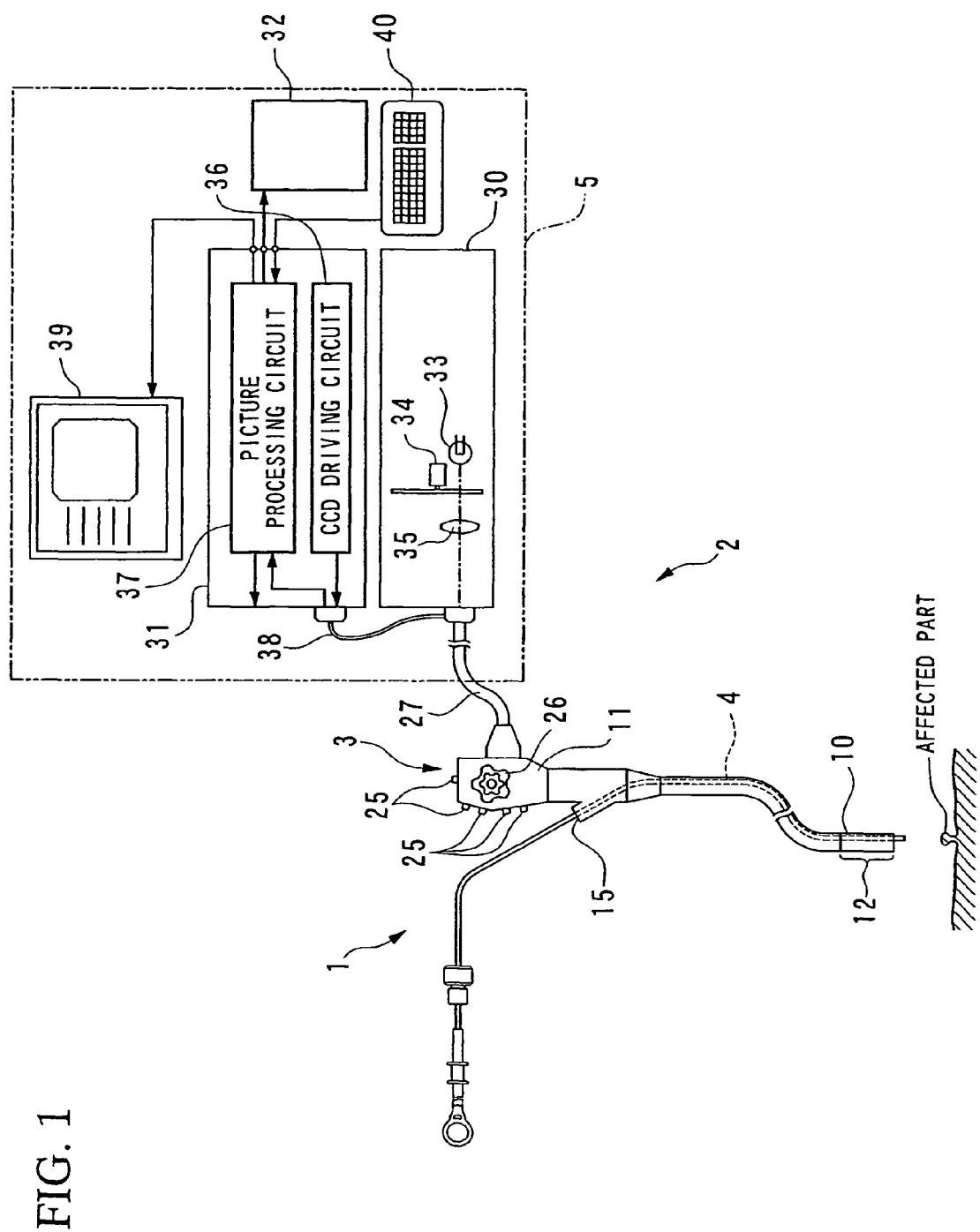
FIG. 1 is a block diagram of an endoscope system for explaining a first embodiment of a medical treatment tool according to the present invention.

As shown in FIG. 1, a medical treatment tool 1 of the present embodiment is inserted into a treatment tool channel 4 of an endoscope device 3, serving as a component of an endoscope system 2, so as to perform a predetermined treatment on a biological tissue in the body. In the present embodiment, the medical treatment tool 1 is described as a ligation unit which ligates the biological tissue. Moreover, the endoscope system 2 comprises an endoscope unit 5 which performs display, recording, and the like of images captured by the endoscope device 3.

Figure 2:
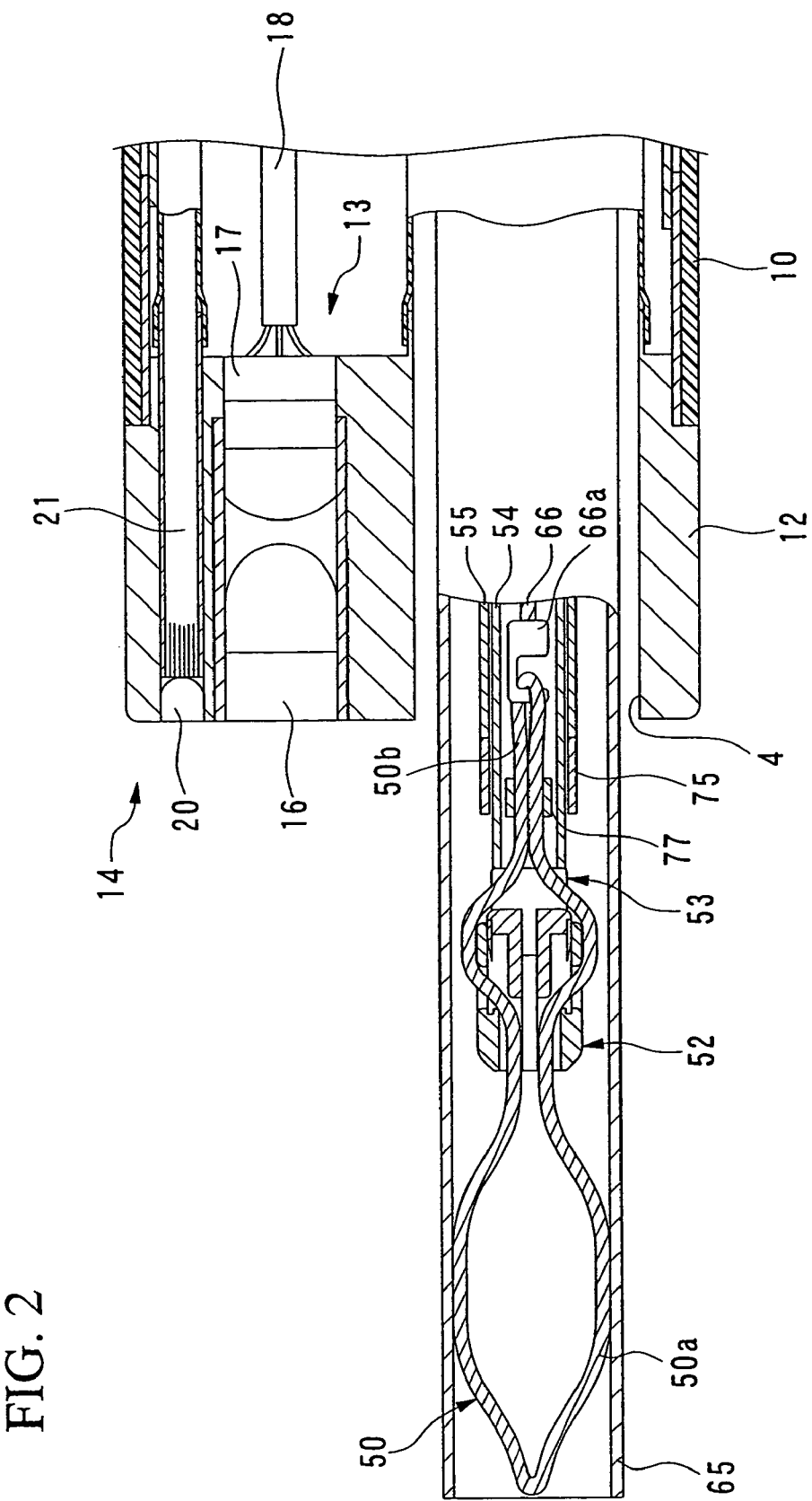
FIG. 2 is a cross-sectional view of a distal end of an endoscope insertion portion of the endoscope device shown in FIG. 1, showing the medical treatment tool inserted into a treatment tool channel.

As shown in FIG. 1 and FIG. 2, the endoscope device 3 comprises a slender endoscope insertion portion 10 which is flexibly curvable to be inserted into the body, and an operation portion 11 which is connected to the proximal end of the endoscope insertion portion 10. The distal end of the endoscope insertion portion 10 is connected with a curvable portion 12, the angle of which is optionally changeable. The distal end of the curvable portion 12 has an observation imaging portion 13 for observing inside the body, and an irradiating portion 14 for irradiating illuminating light supplied from the endoscope unit 5, to inside the body. Moreover, the treatment tool channel 4 is formed in the endoscope insertion portion 10 along the length direction, so as to pass through from a treatment tool through hole 15 provided in the vicinity of the operation portion 11 to the distal end of the endoscope insertion portion 10.

As shown in FIG. 2, the observation imaging portion 13 comprises an observation optical system 16 such as an object lens, which is arranged at the distal end of the endoscope insertion portion 10, that is, the distal end of the curvable portion 12, and an endoscope CCD 17 serving as an individual imager, which is arranged at the imaging position of the observation optical system 16. Moreover, a cable 18 connected to the endoscope CCD 17 is passed through the endoscope insertion portion 10, drawn out to the rear end of the operation portion 11, and connected to the endoscope unit 5.

The irradiating portion 14 has an illumination lens 20 arranged at the distal end of the endoscope insertion portion 10, that is, the distal end of the curvable portion 12, and an LG fiber bundle 21 which is a bundle of optical fibers for guiding illuminating light supplied from the endoscope unit 5 to the illumination lens 20.

As shown in FIG. 1, the operation portion 11 comprises a plurality of switches 25 and an operation knob 26. The switches 25 are programmable switches capable of setting desired functions. For example, one of them functions as a switch which is pushed when recording an endoscopic image captured by the endoscope CCD 17. A signal of this switch 25 is sent to the endoscope unit 5, via a cable 27.

The operation knob 26 is designed to be capable of controlling the direction of the object lens 16, the illumination lens 14, the outlet of the treatment tool channel 4, and the like arranged at the distal end, by curving the curvable portion 12 in optional directions. As a result, inside the body can be observed from optional angles.

The endoscope unit 5 has; a light source unit 30 which supplies the illumination lens 20 with illuminating light, a processor 31 which is connected to the rear end of the cable 18 connected to the endoscope CCD 17, so as to process an imaging signal captured by the endoscope CCD 17, and a recording unit 32 which is connected to the processor 31 to record a picture signal output from the processor 31.

The light source unit 30 has, for example; a lamp 33 which generates white light, a rotating filter 34 attached with color transmission filters of red, blue, and green, to convert the white light emitted from the lamp 33 into an area sequential system, and a condenser lens 35 which collects the area sequential light to be incident into the LG fiber bundle 21. The operation of the lamp 33 is controlled by one of the switches 25 arranged on the operation portion 11.

The processor 31 has a CCD driving circuit 36 which drives the endoscope CCD 17, and a picture processing circuit 37 which performs signal processing on an imaging signal output from the endoscope CCD 17, to generate a picture signal. Moreover, the processor 31 is connected to the cable 27 via the cable 38, so that a CCD driving signal from the CCD driving circuit 36 is sent to the endoscope CCD 17, and an imaging signal from the endoscope CCD 17 is sent to the picture processing circuit 37. Moreover, based on the signal of the switch 25 sent via both cables 38 and 27, the processor 31 outputs the picture signal to the recording unit 32 such as a hard disk, and a monitor 39 such as a display. Furthermore, the processor 31 is connected with an input device 40 such as a keyboard, so that various information such as the examinee's name, ID No., and diagnostic information can be appended to the picture captured by the endoscope CCD 17.

Figure 4:
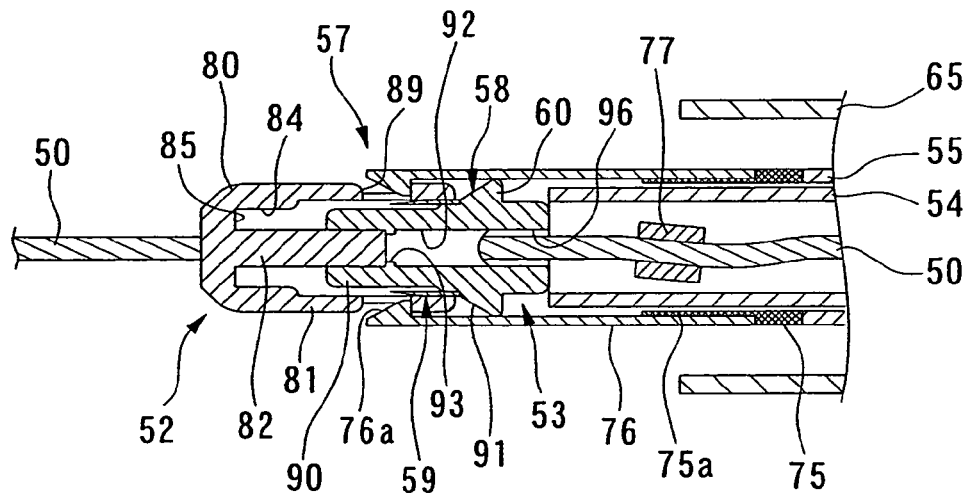
FIG. 4 is a cross-sectional view of a distal end of the medical treatment tool shown in FIG. 3.
Figure 9:
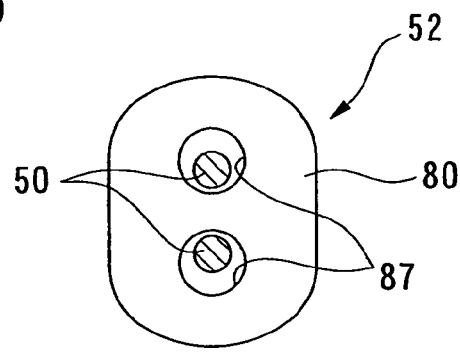
FIG. 9 is a cross-sectional view of the medical treatment tool shown in FIG. 3 taken along the line A-A.
Figure 10:
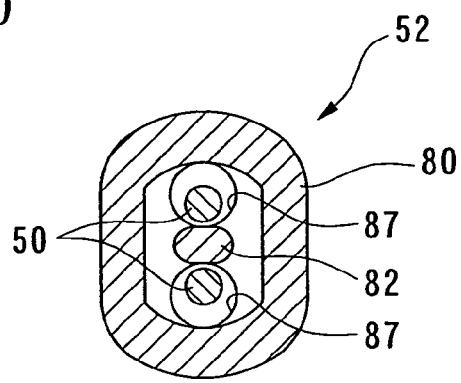
FIG. 10 is a cross-sectional view of the medical treatment tool shown in FIG. 3 taken along the line B-B.
Figure 11:
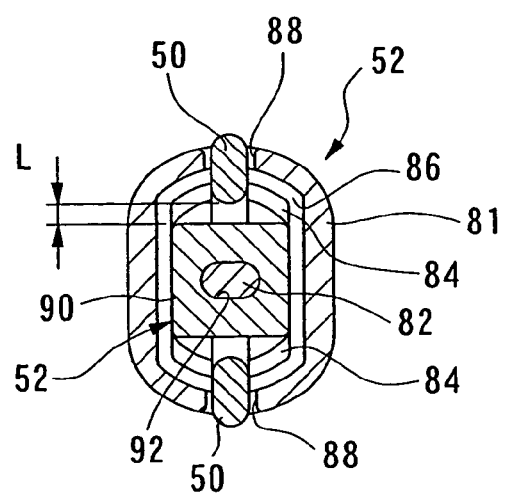
FIG. 11 is a cross-sectional view of the medical treatment tool shown in FIG. 3 taken along the line C-C.
Figure 12:
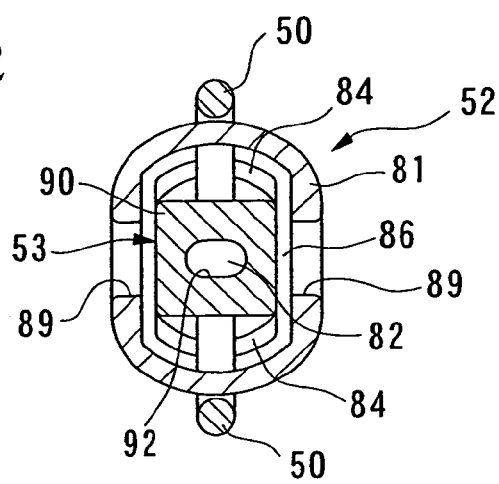
FIG. 12 is a cross-sectional view of the medical treatment tool shown in FIG. 3 taken along the line D-D.
Figure 13:
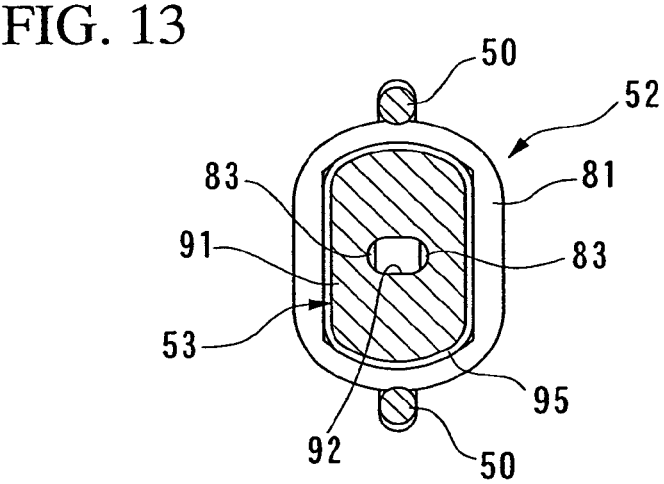
FIG. 13 is a cross-sectional view of the medical treatment tool shown in FIG. 3 taken along the line E-E.
Figure 14:
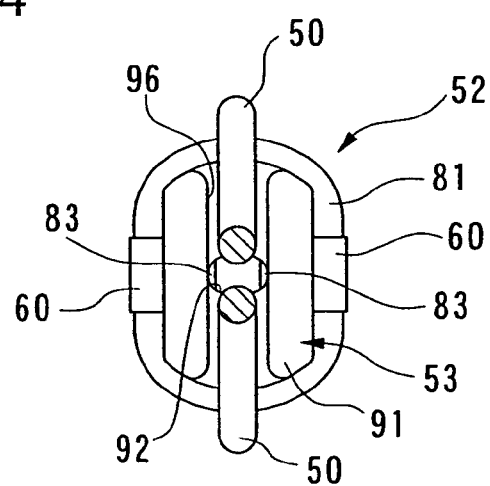
FIG. 14 is a cross-sectional view of the medical treatment tool shown in FIG. 3 taken along the line F-F.

FIG. 3 is a block diagram of the medical treatment tool of the present embodiment shown in FIG. 1. FIG. 4 is a cross-sectional view showing the distal end of the medical treatment tool shown in FIG. 3. FIG. 9 is a cross-sectional view of the medical treatment tool shown in FIG. 3 taken along the line A-A. FIG. 10 is a cross-sectional view of the medical treatment tool shown in FIG. 3 taken along the line B-B. FIG. 11 is a cross-sectional view of the medical treatment tool shown in FIG. 3 taken along the line C-C. FIG. 12 is a cross-sectional view of the medical treatment tool shown in FIG. 3 taken along the line D-D. FIG. 13 is a cross-sectional view of the medical treatment tool shown in FIG. 3 taken along the line E-E. FIG. 14 is a cross-sectional view of the medical treatment tool shown in FIG. 3 taken along the line F-F.

As shown in FIG. 3 and FIG. 4, the medical treatment tool 1 comprises: a flexible ligation wire 50 which performs a predetermined treatment, that is, ligation, on the biological tissue; a wire operation portion 51 which performs a back-and-forth operation of the ligation wire 50; a first member (first wire holding member) 52 which is provided in a back-and-forth movable manner with respect to the ligation wire 50, and holds the ligation wire 50; a second member (second wire holding member) 53 which is provided on the proximal side of the first member 52 in a back-and-forth movable manner in the axial direction, and is capable of holding the ligation wire 50 between itself and the first member 52; a flexible inner sheath (first sheath) 54 which is provided in contact with the proximal side of the second member 53; a flexible engagement sheath (second sheath) 55 which is provided in a back-and-forth movable manner with respect to the inner sheath 54 while covering the inner sheath 54; and an engagement grip (sheath operation portion) 56 which performs a back-and-forth operation of the engagement sheath 55.

Moreover, the first member 52 and the inner sheath 54 have a connection device 57 which connects them to each other. Furthermore, the first member 52 and the second member 53 have a latching device 58 which latches them to each other when holding the ligation wire 50 therebetween, and a cutting device 59 which cuts the ligation wire 50 on the proximal side from the holding position. Furthermore, the second member 53 has coupling catches (connection releasing device) 60 which release the connection of the connection device 57 when latched on the first member 52. These are described in detail later.

Moreover, the medical treatment tool 1 of the present embodiment comprises a medical ligation tool 61 which is to be anchored in the living body, and an operating device 62 which guides the medical ligation tool 61 into the body to perform a ligation operation. Moreover, the operating device 62 comprises a flexible insertion portion 63 to be inserted into the treatment tool channel 4, and a hand-side operation portion 64.

The insertion portion 63 comprises, for example; an outer sheath 65 formed from a flexible plastic such as polyethylene or PTFE, the engagement sheath 55 inserted into the outer sheath 65 in a back-and-forth movable manner, the inner sheath 54 arranged inside of the engagement sheath 55, and an operation wire 66 which is inserted into the inner sheath 54 in a back-and-forth movable manner, and is formed from a metallic strand wire such as stainless steel.

Moreover, the inner sheath 54 and the engagement sheath 55 may be formed from a flexible plastic such as polyethylene or PTFE, similarly to the outer sheath 65, and may have a metallic mesh, or may be a metallic coil sheath.

The hand-side operation portion 64 comprises; an operation portion main body 70 which is connected to the proximal side of the inner sheath 54, a slider 71 which is connected to the proximal side of the operation wire 66, and is back-and-forth movable with respect to the operation portion main body 70 while covering the operation portion main body 70, the engagement grip 56, and a grip 72 which is connected to the proximal side of the outer sheath 65, and performs a back-and-forth operation of the outer sheath 65.

On the proximal side of the operation portion main body 70 is formed a finger catch ring 73. Moreover, the slider 71 has a shape where the center is indented from the opposite ends. As a result, for example, by inserting the thumb into the finger catch ring 73 and holding the slider 71 between the forefinger and the middle finger, the slider 71 can be moved back-and-forth by one hand.

The engagement grip 56 is arranged on the distal side from the operation portion main body 70, so that when operated toward the proximal direction, it is abutted against the distal end of the operation portion main body 70 so as not to be moved in the proximal direction any further. Moreover, the grip 72 is arranged on the distal side from the engagement grip 56. By operating these grip 72, engagement grip 56, and slider 71 back-and-forth, the outer sheath 65, the engagement sheath 55, the inner sheath 54, and the operation wire 66 can be relatively operated.

Figure 5:
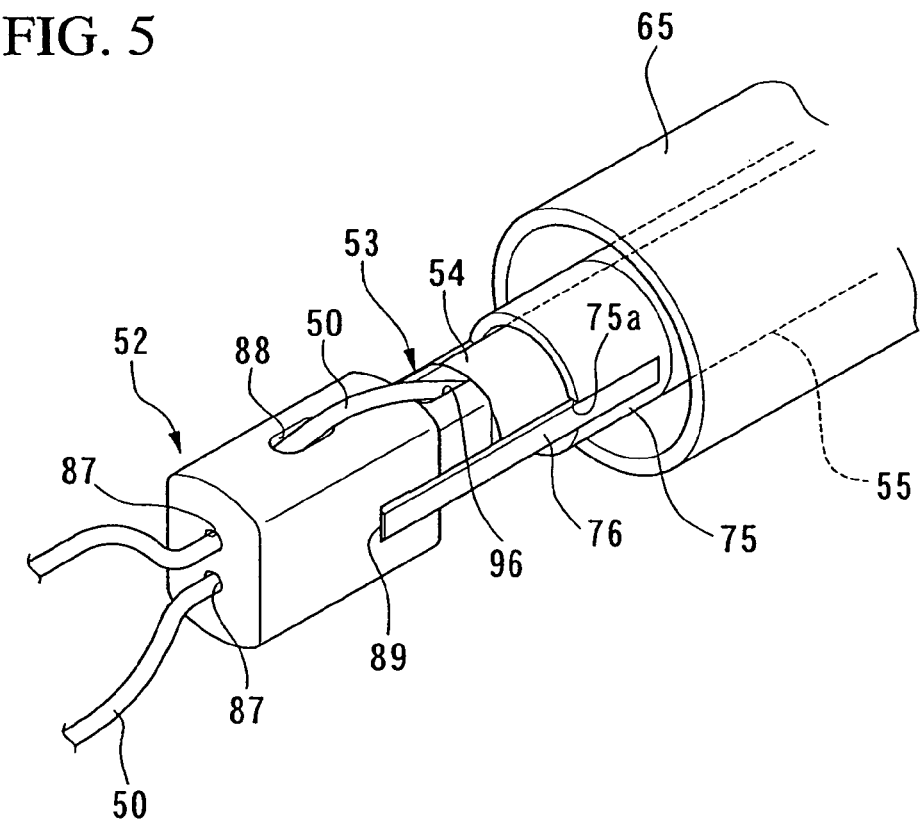
FIG. 5 is a perspective view of the distal end of the medical treatment tool shown in FIG. 3.
Figure 6:
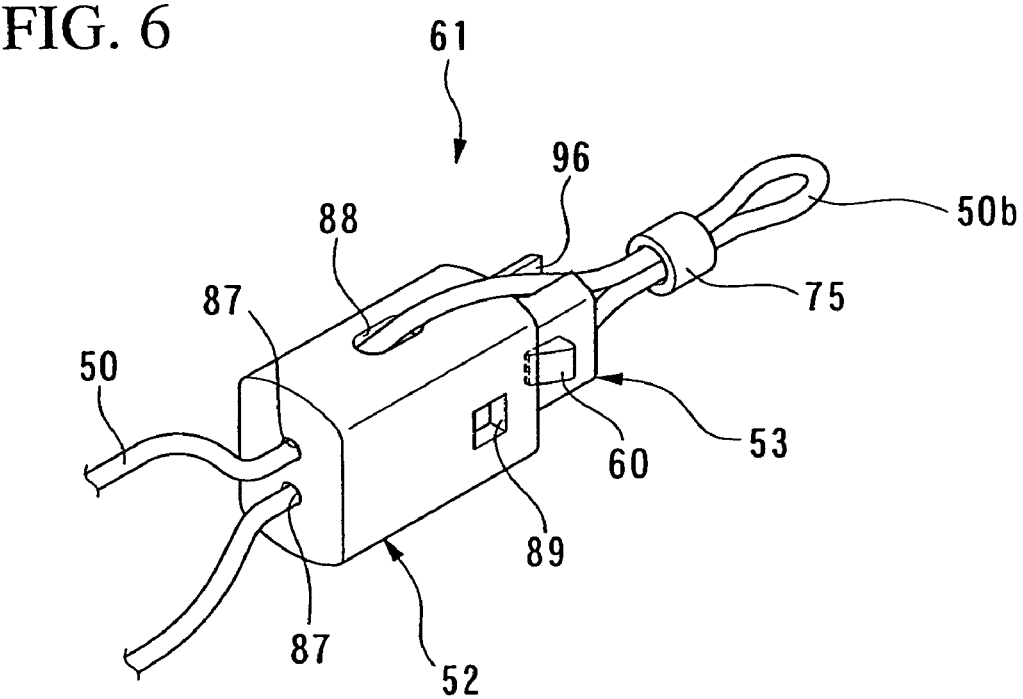
FIG. 6 is a perspective view of a medical ligation tool of the medical treatment tool shown in FIG. 3.
Figure 7:
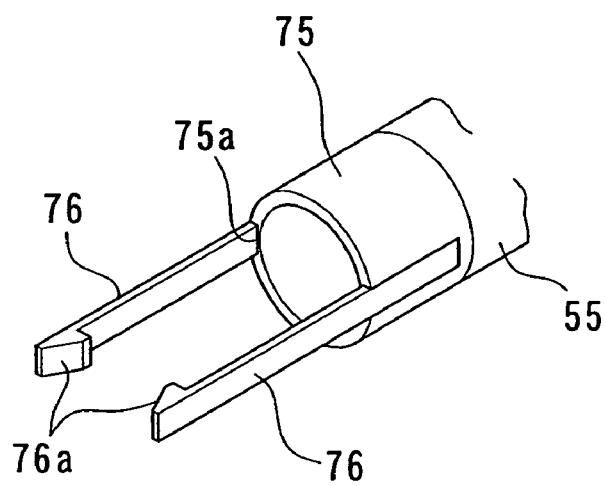
FIG. 7 is a perspective view of linkage hooks provided on a distal end of an engagement sheath.

Moreover, the distal end of the operation wire 66 is affixed with a hook-shaped coupling member 66*a*. Furthermore, as shown in FIG. 4 to FIG. 6, the distal end of the engagement sheath 55 is connected with a linkage pipe 75 that is made from a metallic member such as stainless steel and is formed to have the same outer diameter and inner diameter as those of the engagement sheath 55. Furthermore, the linkage pipe 75 is connected with a pair of linkage hooks (projections) 76, which are projected in the distal direction of the engagement sheath 55, and which have catches 76a projected toward the inside of the engagement sheath 55, on the distal end. The pair of linkage hooks 76 are formed from an elastic metal, plastic, or the like, and are arranged so as to face each other. The linkage hooks 76 are attached to be embedded into grooves 75a in the linkage pipe 75, so as not to cause any step on the outer surface of the linkage pipe 75.

As shown in FIG. 3 to FIG. 5, and FIG. 7 to FIG. 14, the medical ligation tool 61 comprises the ligation wire 50, the first member 52, and the second member 53.

The ligation wire 50 is, for example, a synthetic resin such as nylon or polyolefin, a silk thread, or a bioabsorptive thread, having the distal side as a loop portion 50a. The ligation wire 50 may be in any form of a single wire, a strand wire, or a mesh wire. Moreover, the proximal side of the ligation wire 50 is formed with a folded portion 50b capable of coupling with the coupling member 66a. The opposite ends and two parallel wires of the ligation wire 50 are fixed by a connection pipe 77 serving as a fastening device, by means of adhesion, clamping, or the like.

As a result, by operating the slider 71 back-and forth, the ligation wire 50 can be operated back-and forth via the operation wire 66 and the coupling member 66a. That is, these slider 71, operation wire 66, and coupling member 66a constitute the wire operation portion 51.

The first member 52 is formed in a cylindrical shape having an approximate elliptical cross-section, from a plastic such as polypropylene, ABS, polyacetal, and polycarbonate. The first member 52 is preferably made from a relatively rigid material having superior flowability such as the abovementioned plastic, or liquid crystal polymer or polyphthalamide, however it may be a metal such as stainless steel or aluminum.

The distal side of the first member 52 is provided with a column portion 80, and the proximal side thereof is provided with a cylindrical portion 81 that is integrally molded with the column portion 80. Moreover, in the center of the first member 52 is provided an insertion shaft 82 having an approximate elliptical cross-section, and projected from the distal side toward the proximal side. Furthermore, in the column portion 80, a fixing hollow 84 into which a press-fit portion 90 described later of the second member 53 is press-fitted, is provided so as to surround the insertion shaft 82. The length of the fixing hollow 84 is suitably 1 to 3 mm. Furthermore, the distal end of the fixing hollow 84 is formed with a dead end portion 85 of the press-fit portion 90, and the proximal face of the fixing hollow 84 is formed with dead end faces 86 for cutting blades 95 described later of the second member 53.

Moreover, in the distal face of the first member 52 is formed distal holes 87 through which the ligation wire 50 is inserted one in each. The ligation wire 50 can thus be inserted into the fixing hollow 84 through the distal holes 87. Moreover, on the periphery of the cylindrical portion 81 is formed a pair of side holes 88 which guide the ligation wire 50 that has been inserted into the fixing hollow 84, to the outside of the first member 52. Furthermore, on the periphery of the cylindrical portion 81 is formed a pair of latch holes 89 capable of latching the catches 76a of the linkage hooks 76, in positions rotated by 90 degrees in the circumferential direction about the axis, from the side holes 88.

That is, the latch holes 89 and the linkage hooks 76 constitute the connection device 57.

The second member 53 is formed from a similar material to that of the first member 52, and is formed in a cylindrical shape having an approximate elliptical cross-section. The distal side of this second member 53 is provided with the press-fit portion 90 serving as a small diameter portion, and the proximal side thereof is provided with a large diameter portion 91. Moreover, the center of the second member 53 is provided with a hollow 92 through which the insertion shaft 82 can be inserted in the axial direction. As a result, as described above, the second member 53 can be moved back-and-forth with respect to the first member 52, in the axial direction. In an approximate axial intermediate portion of the hollow 92 is provided a projection 93 so that the insertion shaft 82 cannot easily move toward the proximal direction. The height of the projection 93 is suitably 0.1 mm to 0.3 mm.

The outer diameter of the press-fit portion 90 is set so that it can hold the ligation wire 50 in the fixing hollow 84, when press-fitted into the fixing hollow 84. That is, as shown in FIG. 11, the outer diameter of the press-fit portion 90 is set so that the one-side clearance L between the inner diameter of the fixing hollow 84 and the outer diameter of the press-fit portion 90 is smaller than the outer diameter of the ligation wire 50. This clearance L may be adjusted by the inner diameter of the fixing inner diameter 84 by setting by the outer diameter of the press-fit portion 90. In this manner, the ligation wire 50 can be held between the first member 52 and the second member 53, by means of the press-fit portion 90 and the fixing inner diameter 84.

Moreover, on the periphery of the distal side of the large diameter portion 91, annular cutting blades 95 are set facing the distal direction. These cutting blades 95 are designed to cut the ligation wire 50 on the proximal side from the holding position, when the press-fit portion 90 is abutted against the dead end portion 85 of the first member 52 to hold the ligation wire 50 therebetween. At this time, the distal ends of the cutting blades 95 are abutted against the dead end faces 86.

That is, the cutting blades 95 and the dead end faces 86 constitute the cutting device 59.

Furthermore, on the proximal side of the large diameter portion 91 is formed a pair of slit-shaped wire guides 96 which guide the ligation wire 50 that has been guided to the outside of the first member 52 through the side holes 88, to the inside of the second member 53. The ligation wire 50 that has been guided to the inside by means of the wire guides 96 is inserted into the inner sheath 54, so as to be coupled with the coupling member 66a via the folded portion 50b. Moreover, the periphery of the large diameter portion 91 is provided with a pair of the coupling catches 60 capable of engaging with the latch holes 89 of the first member 52, in positions rotated by 90 degrees in the circumferential direction about the axis, from the wire guides 96. The coupling catches 60 are formed to be projected radially outward from the peripheral face of the large diameter portion 91, so as to be engaged in the latch holes 89 when the press-fit portion 90 is abutted against the dead end portion 85. That is, the coupling catches 60 and the latch holes 89 constitute the latching device 58.

Moreover, when engaged in the latch holes 89, these coupling catches 60 have a function of releasing the connection between the first member 52 and the linkage hooks 76, that is, the connection of the connection device 57, by pushing out the catches 76a of the linkage hooks 76 from the inside of the latch holes 89 to the outside of the first member 52.

Figure 8A:
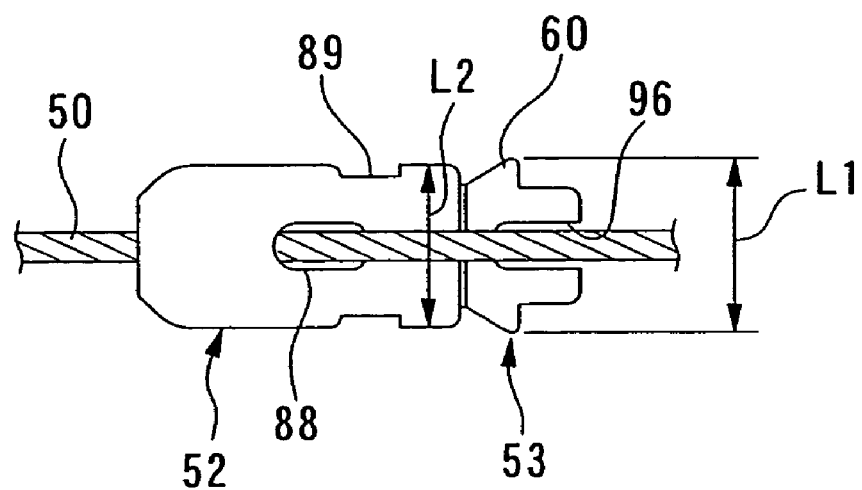
FIG. 8A is a top view of the medical ligation tool shown in FIG. 6.
Figure 8B:
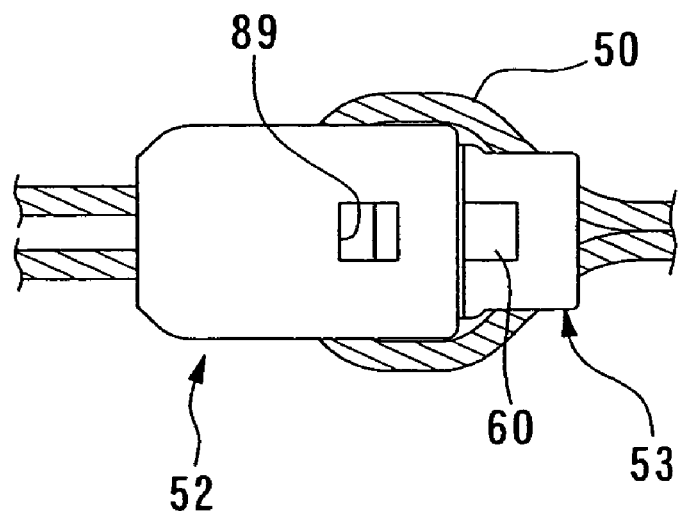
FIG. 8B is a side view of the medical ligation tool shown in FIG. 6.

As shown in FIG. 8, for the coupling catches 60, preferably the distance L1 between the opposite coupling catches 60 is made greater than the distance L2 between the latch holes 89. By so doing, it is possible to reliably push out the catches 76a from the inside of the latch holes 89.

Hereunder is a description of a case where the affected part of the biological tissue inside the body is ligated by the medical treatment tool 1 constituted in such a manner.

Firstly, a desired switch 25 arranged on the operation portion 11 shown in FIG. 1 is pushed to operate the light source unit 30, so as to emit the illuminating light that has been generated from the light source unit 30, from the illumination lens 14 via the LG fiber bundle 21. Moreover, the CCD driving circuit 36 in the processor 31 is operated to drive the endoscope CCD 17.

In this condition, the endoscope insertion portion 10 is inserted into the body of the examinee, for example from the mouth. At this time, by operating the operation knob 26 provided on the operation portion 11, the curvable portion 12 on the distal end of the endoscope insertion portion 10 is inserted while being faced toward a desired direction. By so doing, the endoscope insertion portion 10 can be smoothly inserted into the body, and the illuminating light can be reliably irradiated on a desired position to be observed.

Moreover, an imaging signal captured by the endoscope CCD 17 via the object lens 16, is sent to the processor 31 via the cables 18, 27, and 38, and is converted into a picture signal by the picture processing circuit 37. The converted picture signal is recorded by the recording unit 32, and is sent to the monitor 39 to be displayed as an endoscopic image. At this time, by inputting predetermined information, such as the examinee's name, the examinee's ID No., and the observation site, from the input device 40, it is possible to display it together with the endoscopic image on the monitor 39.

Then, after the doctor confirms by the endoscopic image displayed on the monitor 39, that the distal end of the endoscope insertion portion 10 has reached the affected part to be ligated, he positions the distal end of the endoscope insertion portion 10 in the vicinity of the affected part while watching the monitor 39. Next, in this condition, the doctor inserts the medical treatment tool 1 into the treatment tool channel 4 through the treatment tool through hole 15 of the endoscope device 3. At this time, the doctor moves the grip 72 in the distal direction and inserts the outer sheath 65 into the treatment tool channel 4, in a condition as shown in FIG. 2 where the outer sheath 65 is covered around the loop portion 50a of the ligation wire 50. That is, the loop portion 50a is contained in the outer sheath 65 in a contracted condition.

Moreover, at this time, as shown in FIG. 3 and FIG. 4, since the end of the insertion shaft 82 of the first member 52 is abutted against the projection 93 provided in the hollow 92 of the second member 53, then it is not easily moved toward the proximal direction. As a result, when the medical treatment tool 1 is inserted into the treatment tool channel 4, the first member 52 is not unexpectedly moved toward the second member 53.

Then, after the doctor confirms by the endoscopic image displayed on the monitor 39, that the insertion portion 63 is projected from the distal face of the endoscope insertion portion 10, he moves the grip 72 in the proximal direction, so as to move the outer sheath 65 backward, to a degree that the first member 52 and the second member 53 are exposed. As a result, as shown in FIG. 3, the loop portion 50a of the ligation wire 50 is released from the inside of the outer sheath 65, so that it is elastically restored and the diameter thereof is expanded. After the diameter of the loop portion 50a is expanded, the doctor operates the endoscope while confirming the endoscopic image displayed on the monitor 39, to hook the loop portion 50a on the affected part.

After the loop portion 50a is hooked, the wire operation portion 51 is operated to move the ligation wire 50 in the proximal direction. That is, by moving the slider 71 toward the proximal direction, the operation wire 66 is moved backward, so as to move the ligation wire 50 toward the proximal direction via the coupling member 66a. At this time, since the first member 52 is connected to the engagement sheath 55 by means of the connection device 57, that is, the latch holes 89 and the linkage hooks 76, then only the ligation wire 50 is pulled from the distal holes 87 of the first member 52 into the first member 52. As a result, the diameter of the loop portion 50a is reduced, and the affected part is tightly bound (ligated). By means of this ligation, the blood flow to the affected part can be stopped.

Moreover, as described above, by utilizing the finger catch ring 73, the doctor can readily perform the operation of the slider 71 with one hand, while watching the monitor 39. Furthermore, when the loop portion 50a is hooked, by positioning the first member 52 so as to push against the affected part, the affected part can be readily ligated.

After the doctor confirms by the endoscopic image displayed on the monitor 39, that the affected part is reliably and tightly bound, he moves the engagement grip 56 in the proximal direction, so as to move the engagement sheath 55 backward. As shown in FIG. 4 and FIG. 5, when the engagement sheath 55 is moved backward, since the engagement sheath 55 and the first member 52 are connected by means of the connection device 57, the first member 52 is moved in the proximal direction, that is, toward the second member 53. At this time, the engagement grip 56 is operated with a force to overcome the abutted condition of the projection 93 and the end of the insertion shaft 82 of the first member 52. As a result, the insertion shaft 82 comes over the projection 93, to be inserted into the hollow 92.

Figure 15:
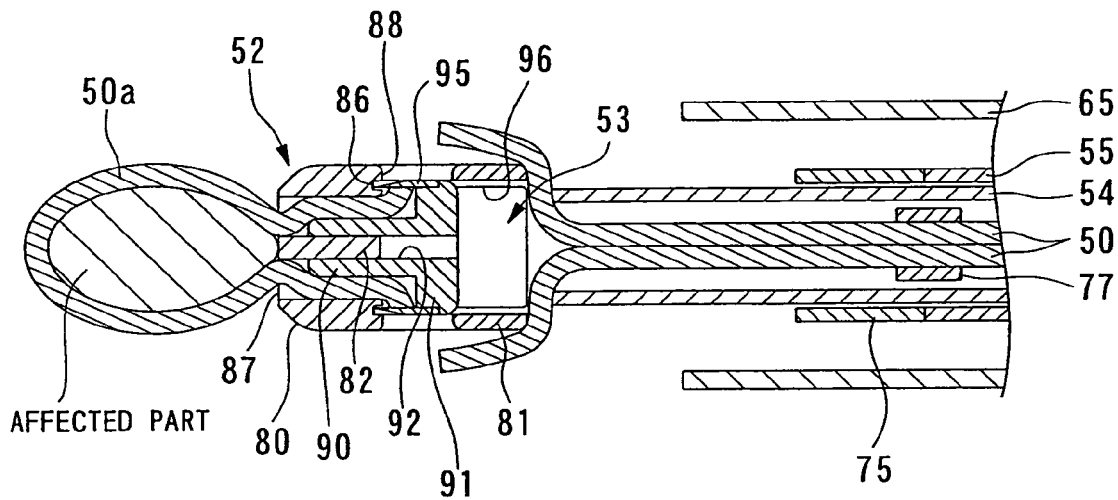
FIG. 15 is a cross-sectional view showing a condition where, after an affected part is ligated by a ligation wire, a first member and a second member are mutually latched to cut the ligation wire.
Figure 16:
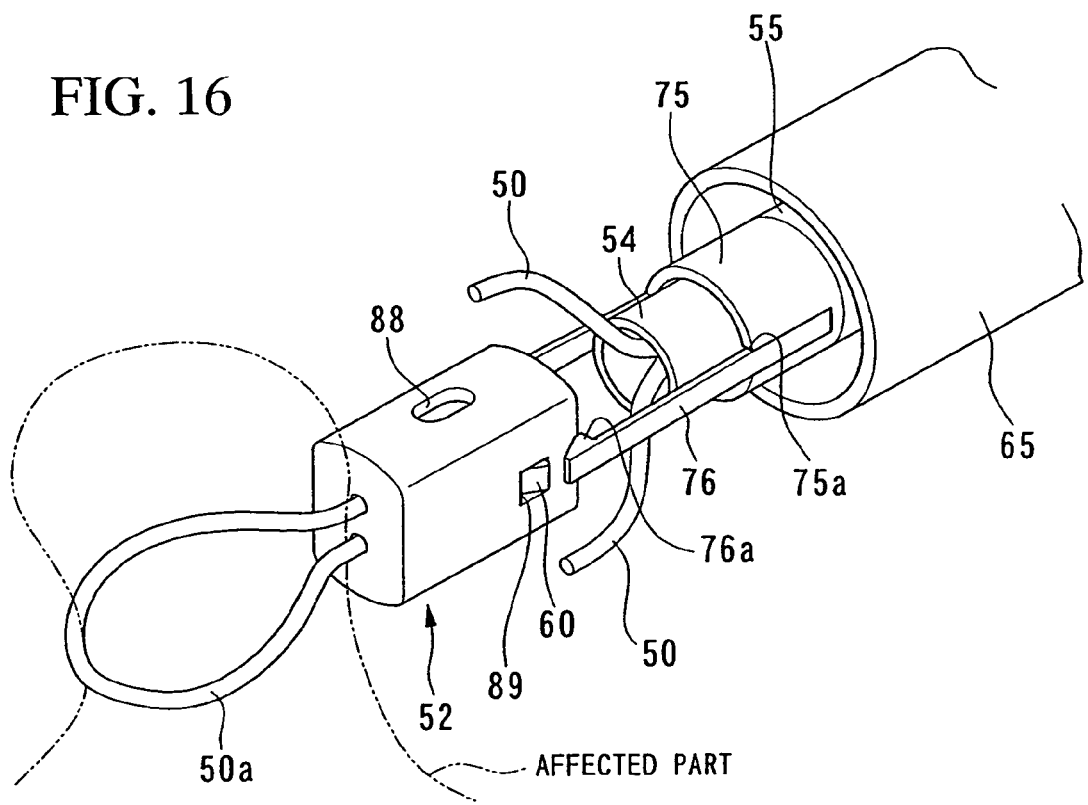
FIG. 16 is a perspective view of the condition shown in FIG. 15.

That is, due to the relative movement, the press-fit portion 90 is moved in the distal direction along the insertion shaft 82, and is press-fitted into the fixing hollow 84. Consequently, the ligation wire 50 in the fixing hollow 84 starts to be held between the inner face of the fixing hollow 84 and the outer face of the press-fit portion 90. Then, due to the further movement, the press-fit portion 90 is abutted against the dead end portion 85, so as to reliably hold and fix the ligation wire 50 therebetween. Moreover, at this time, as shown in FIG. 15 and FIG. 16, the cutting blades 95 of the second member 53 cut the ligation wire 50 on the proximal side of the holding position of the ligation wire 50. After the cutting, the distal end thereof is abutted against the dead end face 86. Moreover, since the cutting blades 95 cut the ligation wire 50 inside the first member 52, the cut ends of the ligation wire 50 are not exposed to the outside of the first member 52.

Figure 17:
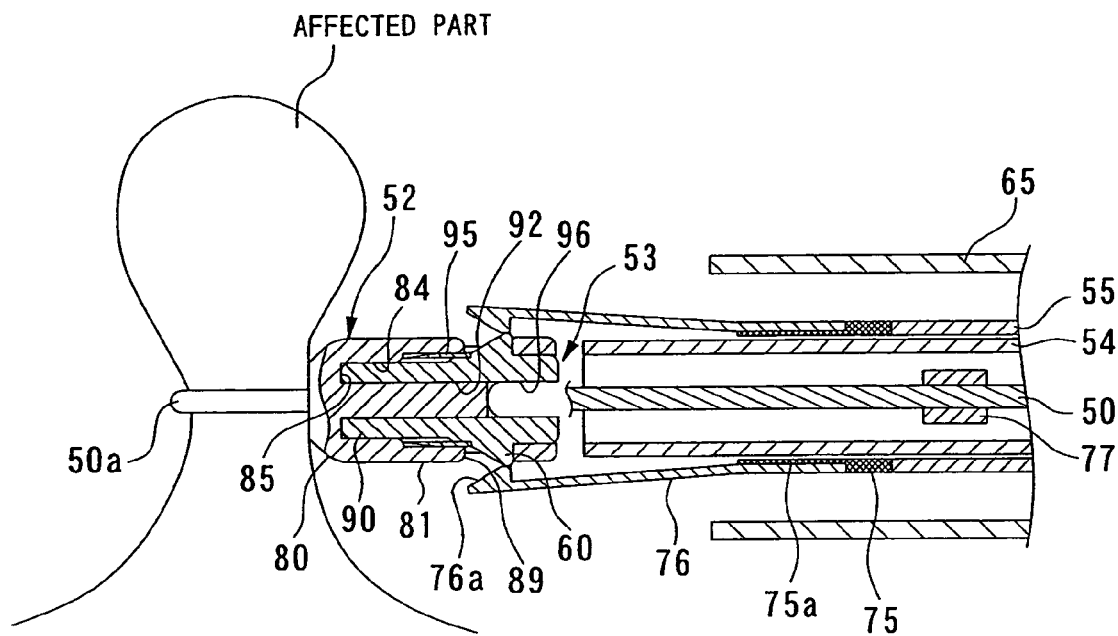
FIG. 17 is a cross-sectional view showing a condition where, in the condition shown in FIG. 15, coupling catches push out linkage catches of a linkage pipe from latch holes, so as to release a connection between the first member and the engagement sheath.

Furthermore, when the press-fit portion 90 is abutted against the dead end portion 85, as shown in FIG. 17, the coupling catches 60 of the second member 53 release the connection of the connection device 57. That is, the coupling catches 60 are engaged into the latch holes 89 of the first member 52, and push out the catches 76a of the linkage hooks 76 to the outside of the first member 52. Moreover, since the coupling catches 60 and the latch holes 89 constitute the latching device 58, the first member 52 and the second member 53 are in the latched condition at the same time.

As described above, the first member 52 and the second member 53 are mutually latched while holding the ligation wire 50 therebetween, and the connection between the linkage hooks 76 and the first member 52 is released.

Figure 18:
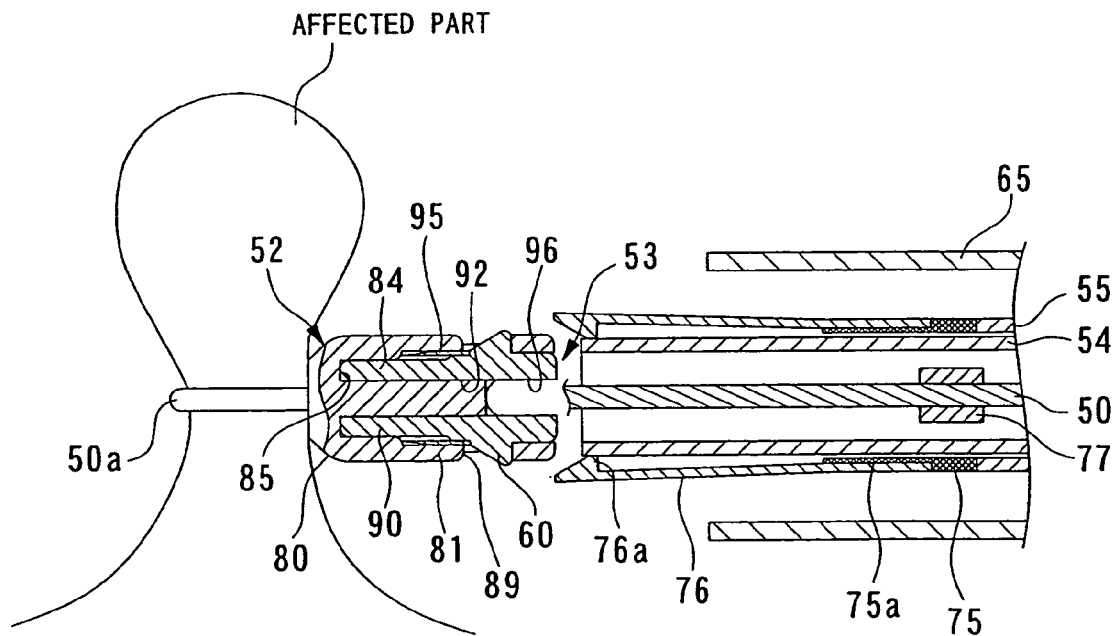
FIG. 18 is a cross-sectional view showing a condition where the engagement sheath is moved backward from the condition shown in FIG. 16.

The doctor watches the endoscopic image displayed on the monitor 39, for example to see that the first member 52 and the second member 53 are mutually latched, and after confirming that the ligation wire 50 is reliably held and cut, he operates the hand-side operation portion 64 so as to slowly separate the distal end of the insertion portion 63 from the affected part. As a result, as shown in FIG. 18, the ligation wire 50 held in the tightly bound condition by the first member 52 and the second member 53, is anchored in the body. As a result, the tight binding treatment of the affected part is completed.

As described above, according to the medical treatment tool 1 of the present embodiment, the first member 52 is moved toward the second member 53 without involving the affected part, so that the ligation wire 50 can be held and fixed between both members 52 and 53, and cut rearward of the holding position. Consequently, since the ligation wire 50 can be reliably held, fixed, and cut, regardless of the condition of the affected part, the operability and the accuracy of the ligation treatment can be improved.

Moreover, since the ligation wire 50 can be held, fixed, and cut, by a series of operations of the engagement grip 56, an effective ligation operation can be performed without taking time.

Furthermore, since the cutting blades 95 cut the ligation wire 50 inside the first member 52, so as not to expose the cut ends of the ligation wire 50 to the outside of the first member 52, interference with other treatment tools or the endoscope insertion portion 10 can be prevented.

Moreover, since the cutting blades 95 are provided on the second member 53 serving as the medical ligation tool 61, the cutting blades 95 are not repeatedly used. Consequently, since the cutting blades 95 are always in a new condition, their sharpness does not decrease.

Furthermore, since the latching device 58 is constituted by utilizing the latch holes 89 of the connection device 57 and the coupling catches 60 serving as the connection releasing device, it is not necessary to separately provide an exclusive latching device. Consequently, the structure can be simplified.

Next, hereunder is a description of a second embodiment of a medical treatment tool according to the present invention, with reference to FIG. 19 to FIG. 35. In this second embodiment, the same reference symbols are used for components the same as those in the first embodiment, and description thereof is omitted.

Figure 19:
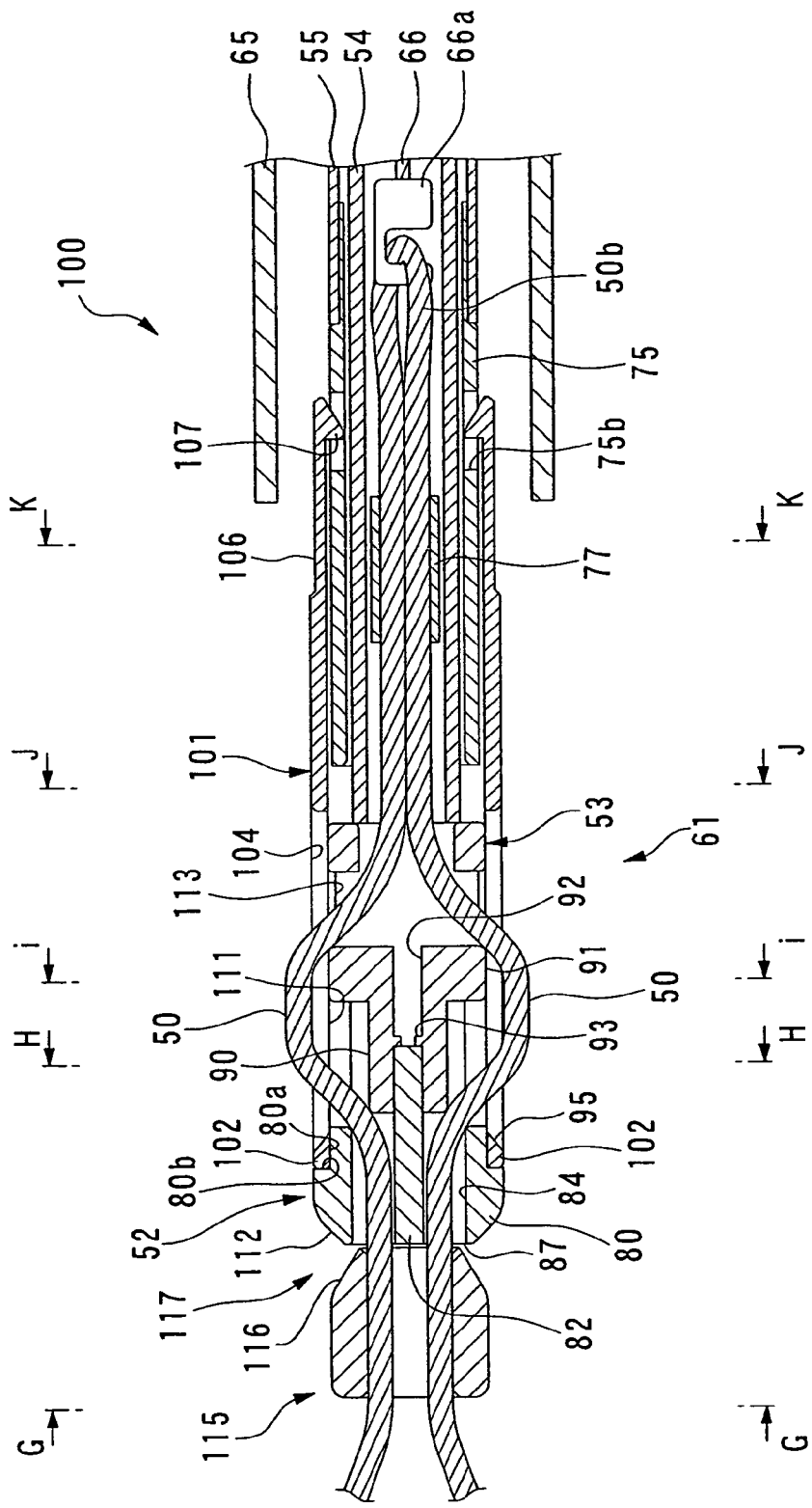
FIG. 19 is a cross-sectional view in the vicinity of a medical ligation tool showing a second embodiment of the medical treatment tool of the present invention.
Figure 26:
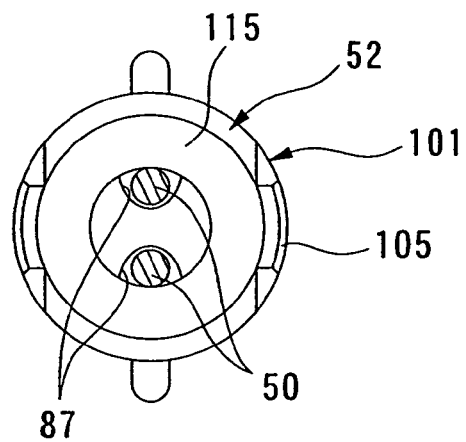
FIG. 26 is a cross-sectional view of the medical treatment tool shown in FIG. 19 taken along the line G-G.
Figure 27:
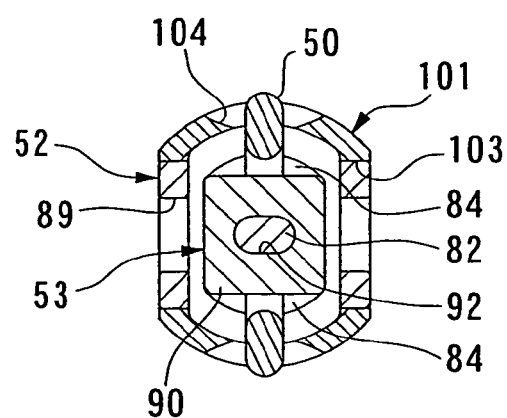
FIG. 27 is a cross-sectional view of the medical treatment tool shown in FIG. 19 taken along the line H-H.
Figure 28:
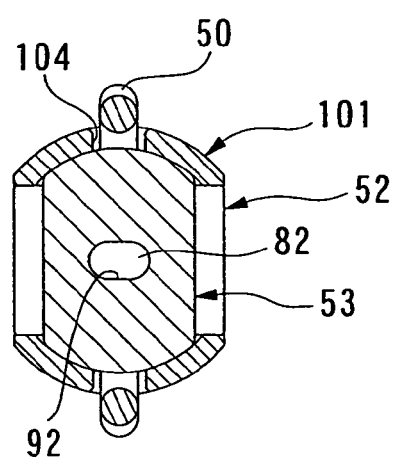
FIG. 28 is a cross-sectional view of the medical treatment tool shown in FIG. 19 taken along the line i-i.
Figure 29:
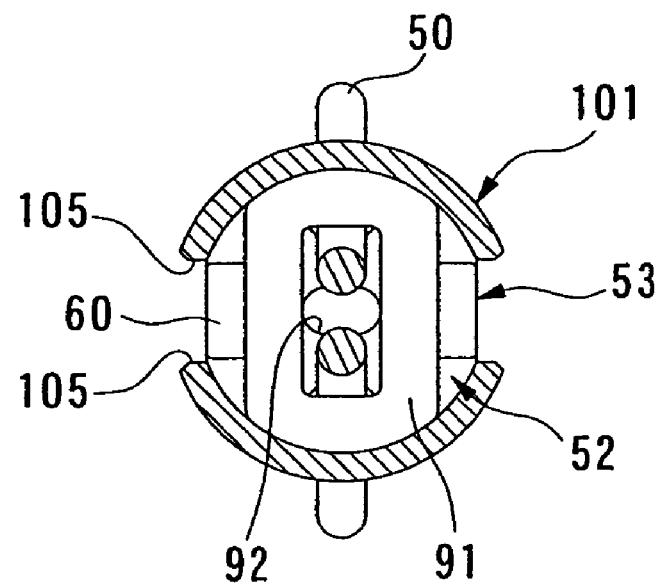
FIG. 29 is a cross-sectional view of the medical treatment tool shown in FIG. 19 taken along the line J-J.
Figure 30:
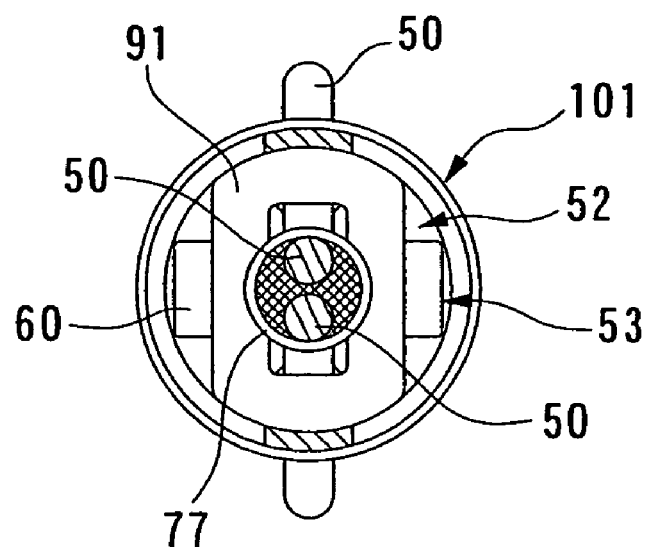
FIG. 30 is a cross-sectional view of the medical treatment tool shown in FIG. 19 taken along the line K-K.

FIG. 19 is a cross-sectional view in the vicinity of a medical ligation tool showing the second embodiment of the medical treatment tool of the present invention. FIG. 26 is a cross-sectional view of the medical treatment tool shown in FIG. 19 taken along the line G-G. FIG. 27 is a cross-sectional view of the medical treatment tool shown in FIG. 19 taken along the line H-H. FIG. 28 is a cross-sectional view of the medical treatment tool shown in FIG. 19 taken along the line i-i. FIG. 29 is a cross-sectional view of the medical treatment tool shown in FIG. 19 taken along the line J-J. FIG. 30 is a cross-sectional view of the medical treatment tool shown in FIG. 19 taken along the line K-K.

The point where the second embodiment is different to the first embodiment is that in the medical treatment tool 1 of the first embodiment, the cutting blades 95 are provided on the second member 53, so as to hold and cut the ligation wire 50 at the same time, whereas in the medical treatment tool 100 of the second embodiment, a cutting member 101 having the cutting blades 95 is provided separately from the second member 53, so that the ligation wire 50 is cut by the cutting member 101, after the first member 52 and the second member 53 are latched.

That is, as shown in FIG. 19 to FIG. 30, the medical treatment tool 100 of the present embodiment comprises the cutting member 101 which is provided on the distal end of the engagement sheath 55, and in which the cutting blades 95 for cutting the ligation wire 50 on the proximal side from the holding position where it is held between the first member 52 and the second member 53, are arranged on the distal side from the ligation wire 50. The cutting member 101 is formed from a metal such as stainless steel, in an approximate cylindrical shape, so as to cover the linkage pipe 75 and the second member 53, and is formed to have the same outer diameter as that of the first member 52. On the distal side of the cutting member 101 is formed distal slits 103 so that the distal end is forked into two so as to project a pair of distal arms 102 in the distal direction. In the center of the outer surface of the distal arms 102 is formed an axially extended wire slit 104, so that the ligation wire 50 that has been exposed to the outside between the first member 52 and the second member 53 can be inserted into the wire slit 104. Moreover, the distal arms 102 are designed to be engaged into arm receivers 80a described later, that are formed on the proximal side of the column portion 80 of the first member 52. Furthermore, on the distal edge of each wire slit 104 is formed the cutting blade 95. As a result, the cutting blade 95 is arranged on the distal side from the ligation wire 50. As shown in FIG. 19, each cutting blade 95 is formed so as not to be projected to the proximal side from the arm receivers 80a, when the distal end of the distal arm 102 is abutted against the dead end face 80b of the arm receiver 80a.

Moreover, the distal slit 103 is formed in a size which does not interfere with the latch hole 89 of the first member 52 and the coupling catch 60 of the second member 53. Furthermore, the proximal side of the distal slit 103 is formed with a hooking slit 105 extended further in the proximal direction, so as not to interfere with the linkage hook 76.

Moreover, on the proximal side of the cutting member 101 is formed a pair of linkage arms 106 so as to be extended in the proximal direction, on the same axes as those of the wire slits 104. Furthermore, the distal end of each linkage arm 106 is formed with a linkage catch 107 projected radially inward.

Moreover, on the outer surface of the linkage pipe 75 of the present embodiment is formed a pair of linkage holes 75b capable of engaging with the linkage catches 107. That is, these linkage holes 75b are formed in the proximal side of the linkage pipe 75, in positions rotated by 90 degrees in the circumferential direction about the axis, from the linkage hooks 76.

That is, by engaging the linkage catches 107 of the linkage arms 106 into the linkage holes 75b, the cutting member 101 can be connected to the linkage pipe 75, and attached in the distal direction of the engagement sheath 55. In this manner, the cutting member 101 becomes attachable/detachable to the engagement sheath 55 by means of the linkage arms 106.

Figure 22:
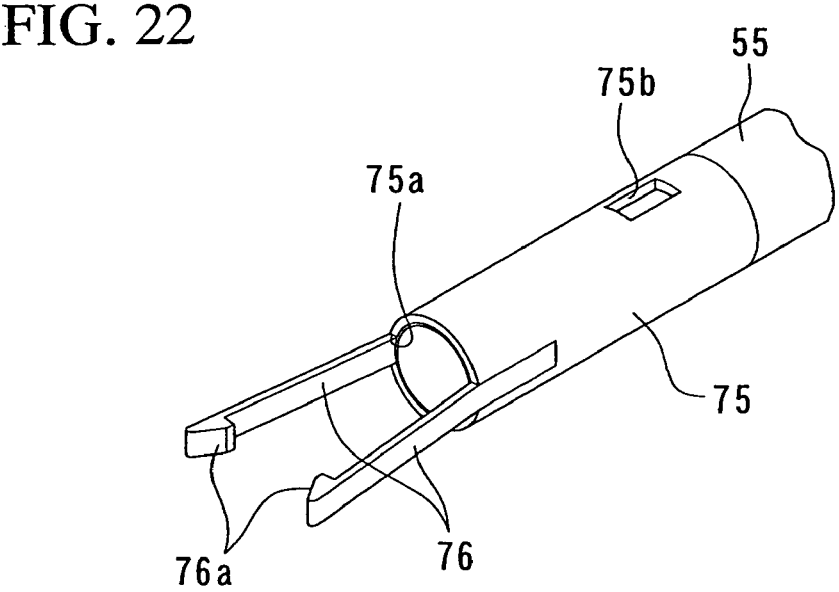
FIG. 22 is a perspective view showing linkage hooks provided on a distal end of an engagement sheath of the medical treatment tool shown in FIG. 19.

As shown in FIG. 22, the linkage hole 75b is in a rectangular shape that is long in the axial direction. It is designed such that, as shown in FIG. 19, when the distal ends of the distal arms 102 are abutted against the dead end faces 80b of the arm receivers 80a, the linkage catches 107 are positioned in the approximate centers of the linkage holes 75b. That is, in the condition where the linkage catches 107 are engaged in the linkage holes 75b, the engagement sheath 55 can be slightly moved in the axial direction.

Moreover, as mentioned above, in the first member 52 of the present embodiment, the proximal side of the column portion 80 is formed with reduced diameter arm receivers 80a, and the side faces on the distal sides of the outer diameter arm receivers 80a become the dead end faces 80b. The outer diameter of the arm receivers 80a is set so as not to cause any step between the outer diameter of the first member 52 and the outer diameter of the distal arms 102. Furthermore, the first member 52 is formed with slits 111 in the cylindrical portion 81, so that the ligation wire 50 is guided through the slits 111, from the inside of the fixing hollow 84 to the outside of the first member 52. Moreover, the distal end of the first member 52 is formed with a tapered portion 112 so that the diameter is gradually decreased toward the distal direction.

Furthermore, in the second member 53 of the present embodiment, an approximate middle portion of the large diameter portion 91 is formed with a pair of side holes 113 for guiding the ligation wire 50 that has been guided to the outside of the first member 52 through the slits 111, to the inside of the second member 53. The ligation wire 50 guided to the inside through the side holes 113, is inserted into the inner sheath 54, and coupled with the coupling member 66a via the folded portion 50b.

Moreover, on the distal end of the first member 52 is arranged a tubular member 115 formed in a cylindrical shape, from a metal such as stainless steel, or a plastic material such as ABS or a silicon resin. The ligation wire 50 is inserted into the first member 52 through the distal holes 87 of the first member 52, after being passed through the tubular member 115. Moreover, on the proximal side of the tubular member 115 is formed a tapered portion 116 so that the diameter is gradually decreased toward the proximal direction. The tapered portion 116 and the tapered portion 112 of the first member 52 constitutes an annular concavity 117.

In the present embodiment, this tubular member 115 is also a part of the components of the medical ligation tool 61.

Figure 23:
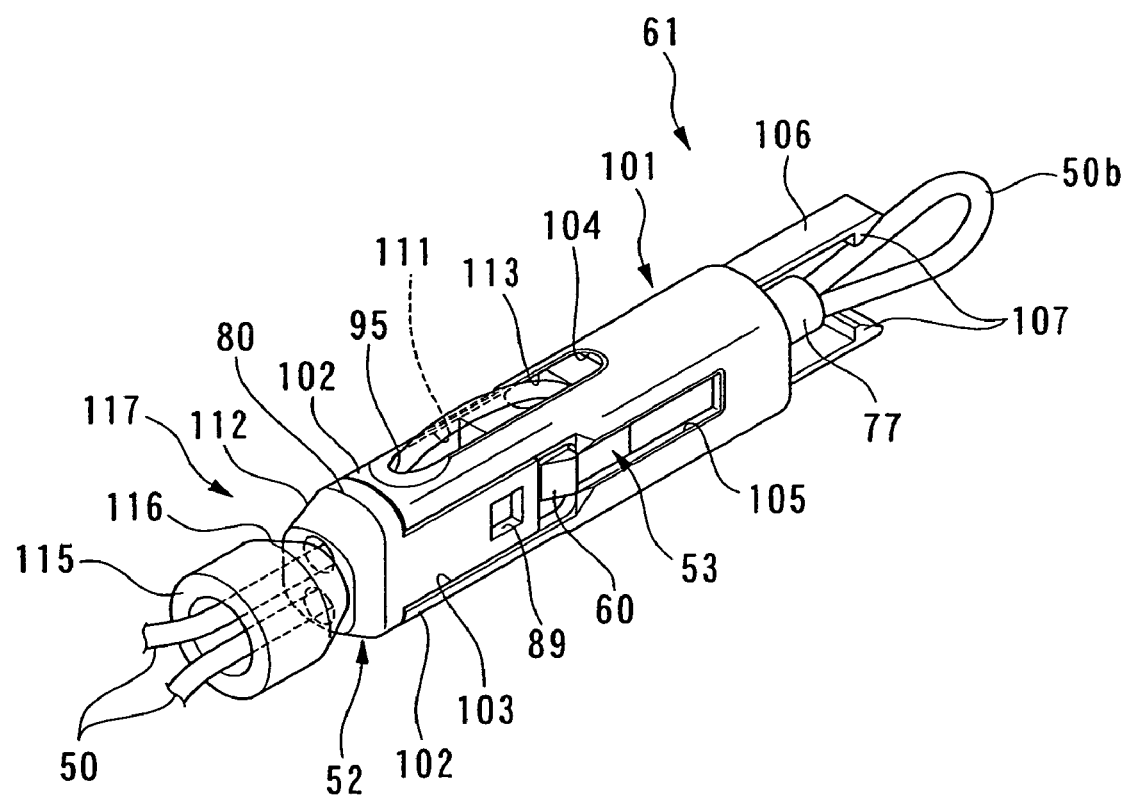
FIG. 23 is a perspective view of the medical ligation tool of the medical treatment tool shown in FIG. 19.
Figure 24:
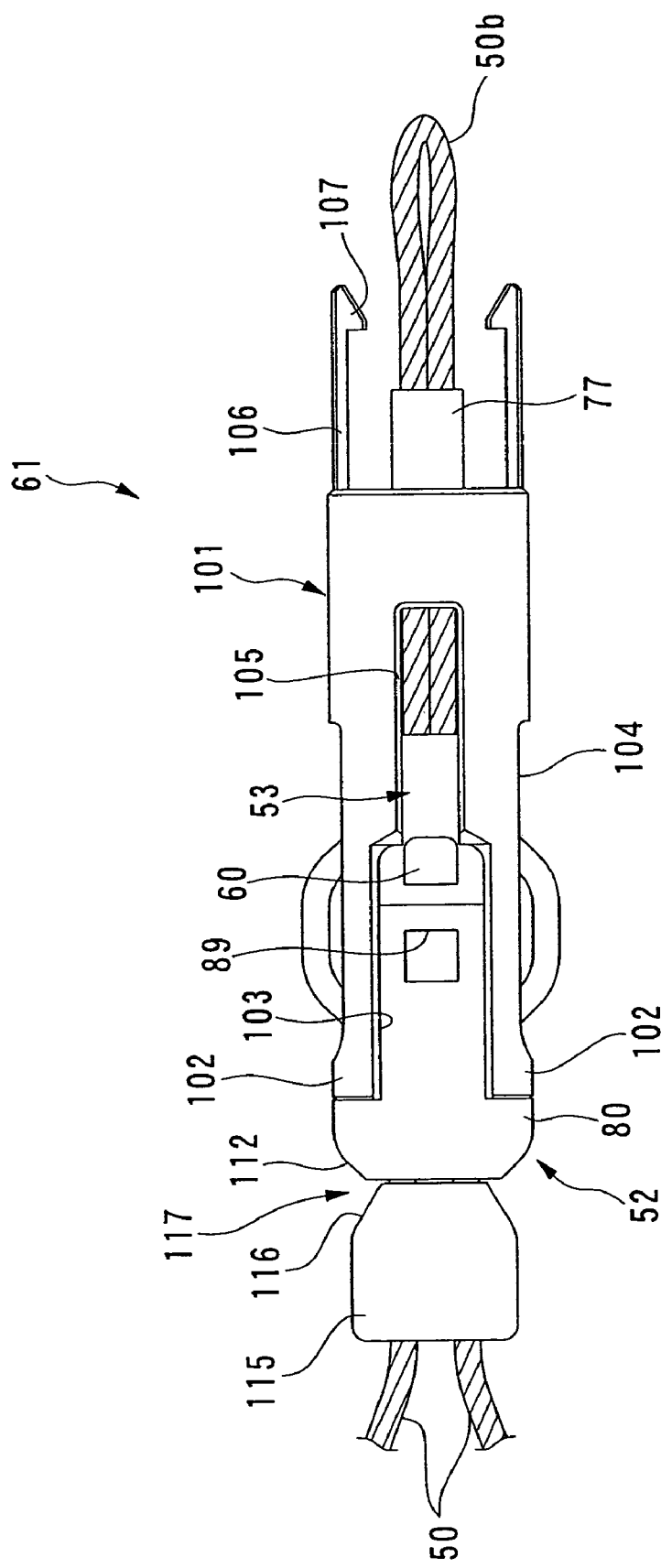
FIG. 24 is a top view of the medical ligation tool shown in FIG. 23.
Figure 25:
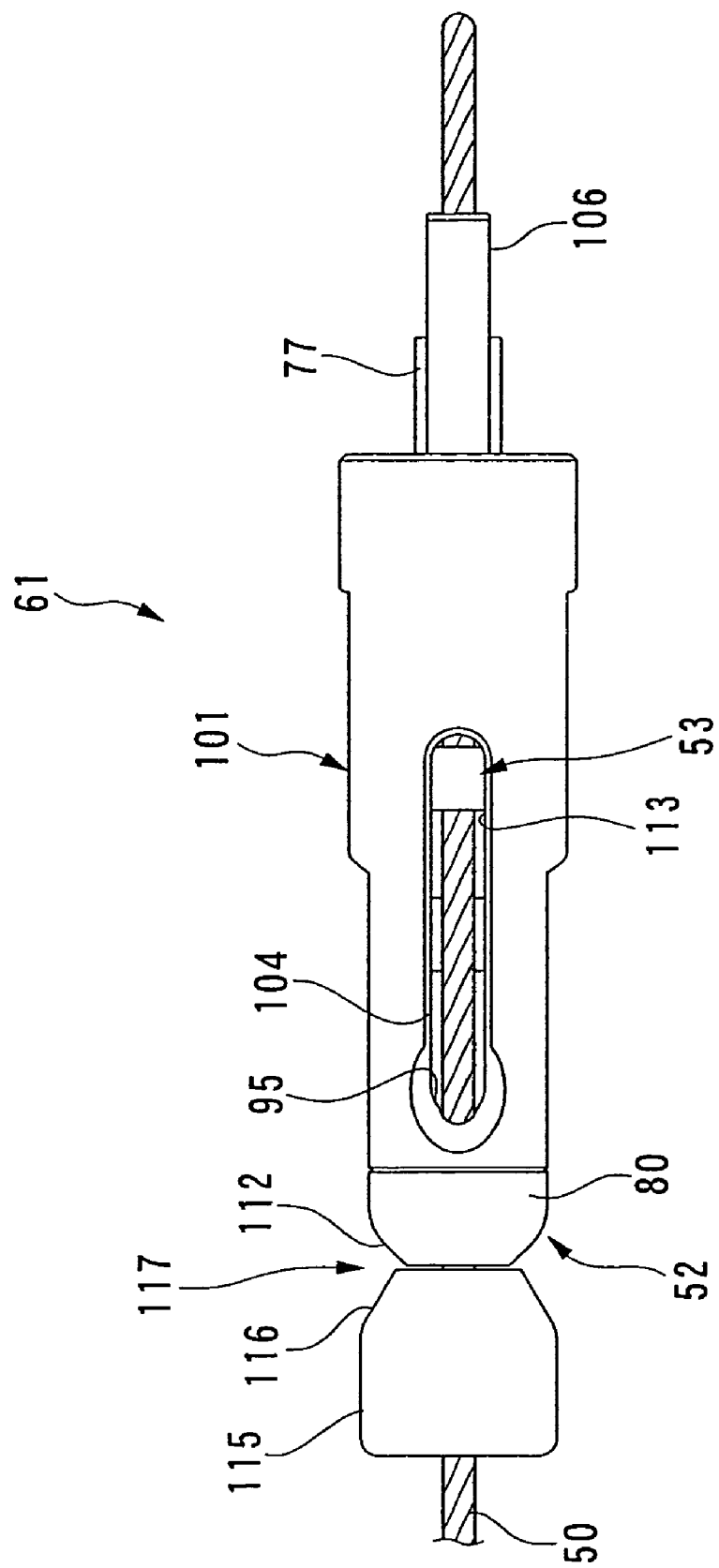
FIG. 25 is a side view of the medical ligation tool shown in FIG. 23.

Moreover, in the present embodiment, firstly, the medical ligation tool 61, that is, the ligation wire 50, the tubular member 115, the first member 52, and the second member 53 are combined. Then as shown in FIG. 23 to FIG. 25, the cutting member 101 is attached to the medical ligation tool 61. That is, the cutting member 101 is inserted from the distal arm 102 side so as to cover the second member 53 side, and the distal ends of the distal arms 102 are abutted against the dead end faces 80b of the arm receivers 80a of the first member 52, and attached thereto. At this time, by pushing and stretching the distal arms 102 outward, the ligation wire 50 can be readily inserted into the wire slits 104. The ligation wire 50 may be attached after the first member 52, the second member 53, and the cutting member 101 have been previously combined.

Hereunder is a description of a case where the affected part of the biological tissue inside the body is ligated by the medical treatment tool 100 constituted in such a manner.

The slider 71 is moved in the distal direction, so as to project the coupling member 66a from the distal opening of the inner sheath 54. In this condition, the folded portion 50b of the ligation wire 50 is hooked on the coupling member 66a. After it is hooked, the slider 71 is moved in the proximal direction, to pull the coupling member 66a into the inner sheath 54, and to insert the cutting member 101 so as to cover the periphery of the linkage pipe 75, and then the linkage catches 107 of the linkage arms 106 are engaged into the linkage holes 75b.

Figure 21:
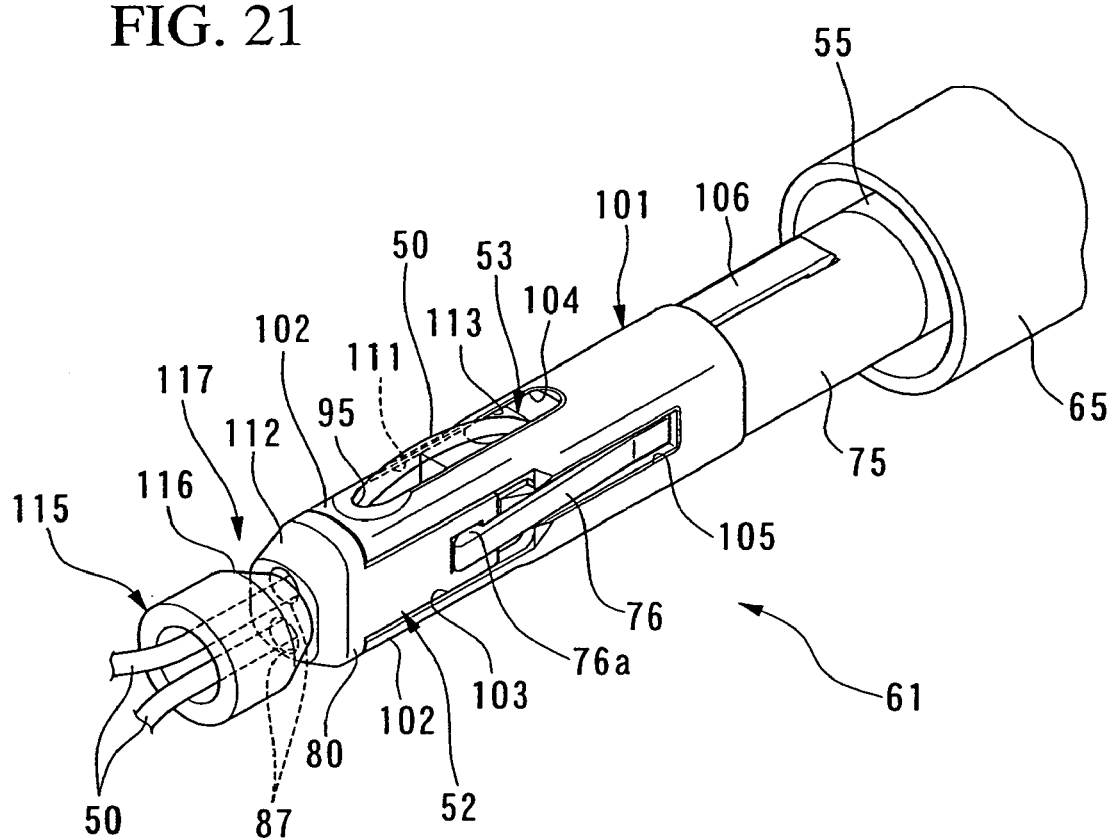
FIG. 21 is a perspective view of the medical treatment tool shown in FIG. 19.

Moreover, at this time, as shown in FIG. 21, the linkage hooks 76 of the engagement sheath 55 are once taken out from the hooking slits 105 to the outside of the cutting member 101, and then are engaged into the latch holes 89 of the first member 52.

Figure 20:
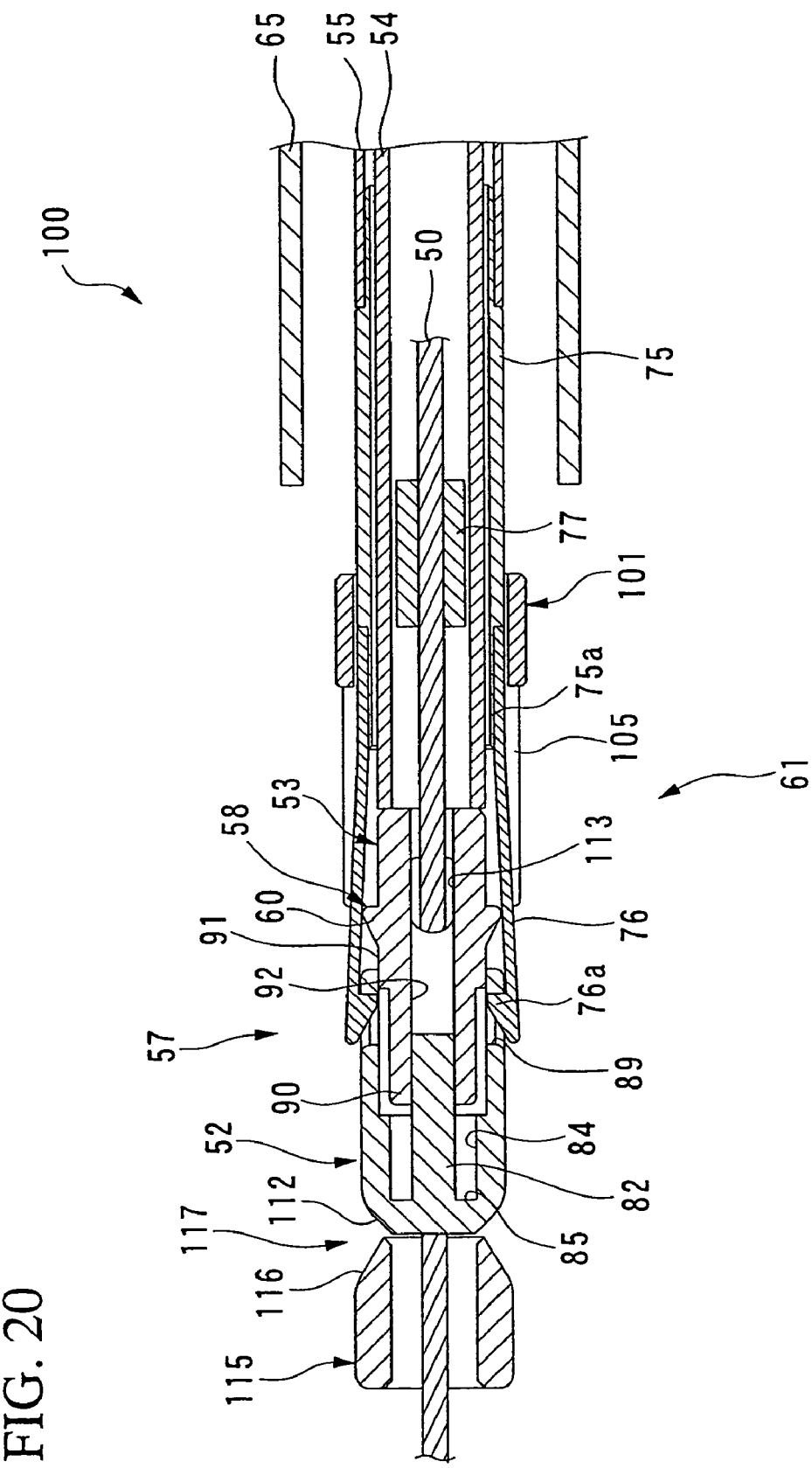
FIG. 20 is a cross-sectional view of the medical treatment tool shown in FIG. 19, viewed from the side.

As a result, as shown in FIG. 19 to FIG. 21, the first member 52 and the engagement sheath 55 are mutually connected by means of the connection device 57, and the engagement sheath 55 and the cutting member 101 are mutually connected by means of the linkage catches 107 and the linkage holes 75b.

Then, the doctor operates the endoscope while watching the endoscopic image displayed on the monitor 39, and hooks the loop portion 50a on the affected part. After the loop portion 50a is hooked, by moving the slider 71 toward the proximal direction, the operation wire 66 is moved backward, so as to move the ligation wire 50 toward the proximal direction via the coupling member 66a. At this time, since the first member 52 is connected to the engagement sheath 55 by means of the connection device 57, that is, the latch holes 89 and the linkage hooks 76, then only the ligation wire 50 is pulled from the distal holes 87 of the first member 52 into the first member 52. Moreover, since the first member 52 is not moved, the cutting member 101 is also not moved. As a result, the diameter of the loop portion 50a is reduced, and the affected part is tightly bound (ligated). By means of this ligation, the blood flow to the affected part can be stopped.

Furthermore, when the loop portion 50a is hooked, by positioning the tubular member 115 so as to push against the affected part, the affected part can be readily ligated.

After the affected part is tightly bound, the engagement grip 56 is moved in the proximal direction, so as to move the engagement sheath 55 backward. When the engagement sheath 55 is moved backward, since the engagement sheath 55 and the first member 52 are connected by means of the connection device 57, the first member 52 is moved in the proximal direction, that is, toward the second member 53. Moreover, since the distal ends of the distal arms 102 of the cutting member 101 are abutted against the dead end faces 80b, the cutting member 101 is also pushed together with the movement of the first member 52 in the proximal direction, and integrally moved in the proximal direction. In this case, since the relative position of the first member 52 and the cutting member 101 is not changed, the cutting blades 95 do not come out from the arm receivers 80b to the proximal side.

Similarly to the first embodiment, the engagement grip 56 is operated with a force to overcome the abutted condition of the projection 93 and the end of the insertion shaft 82 of the first member 52, so that the insertion shaft 82 comes over the projection 93, to be inserted into the hollow 92.

Figure 31:
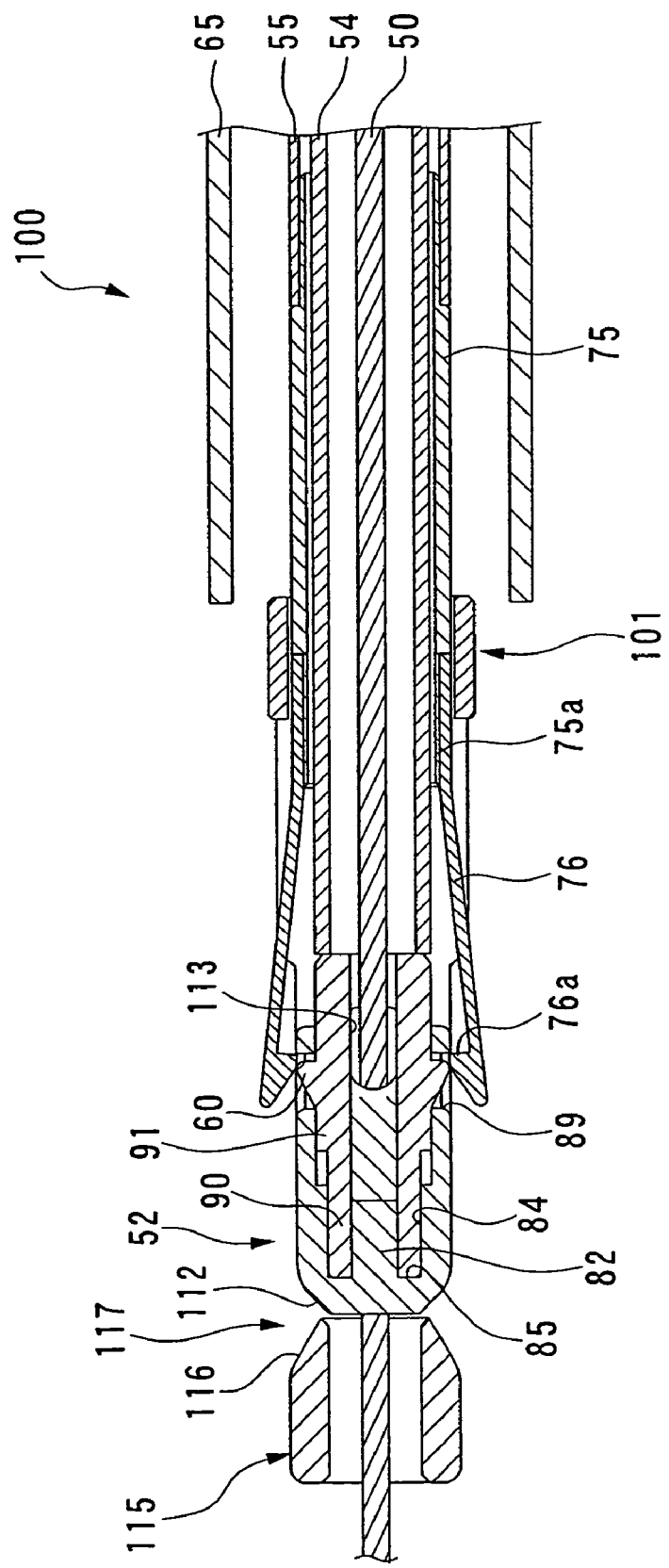
FIG. 31 is a cross-sectional view showing a condition where, after an affected part is ligated by a ligation wire, the first member and the second member are mutually latched to hold the ligation wire therebetween, and a condition where coupling catches push out linkage catches of a linkage pipe from latch holes, so as to release a connection between the first member and the engagement sheath.
Figure 32:
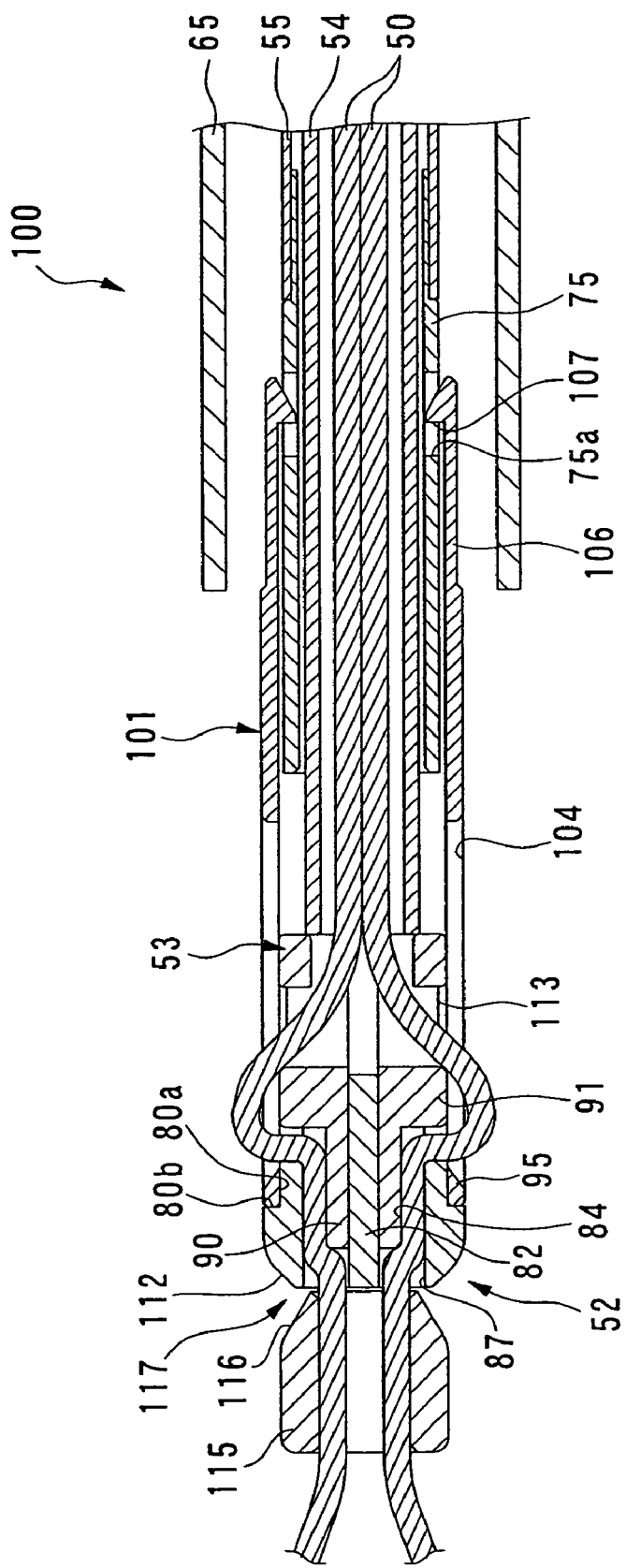
FIG. 32 is a cross-sectional view showing the ligation wire in the condition shown in FIG. 31.

Due to the movement of the first member 52, the press-fit portion 90 is moved in the distal direction along the insertion shaft 82, and is press-fitted into the fixing hollow 84, and the ligation wire 50 in the fixing hollow 84 starts to be held between the inner face of the fixing hollow 84 and the outer face of the press-fit portion 90. Then, due to the further movement, as shown in FIG. 31 and FIG. 32, the press-fit portion 90 is abutted against the dead end portion 85, so as to reliably hold and fix the ligation wire 50 therebetween. At this time, as shown in FIG. 32, the ligation wire 50 is in a condition where it comes out from the slits 111 of the first member 52 into the wire slits 104 of the cutting member 101, on the proximal side of the holding position.

Moreover, as shown in FIG. 31, the coupling catches 60 of the second member 53 are engaged into the latch holes 89 of the first member 52, and push out the catches 76a of the linkage hooks 76 to the outside of the first member 52. Furthermore, since the coupling catches 60 and the latch holes 89 constitute the latching device 58, the first member 52 and the second member 53 are in the latched condition at the same time. That is, the first member 52 and the second member 53 are mutually latched while holding the ligation wire 50 therebetween, and the connection between the linkage hooks 76 and the first member 52 is released.

Figure 33:
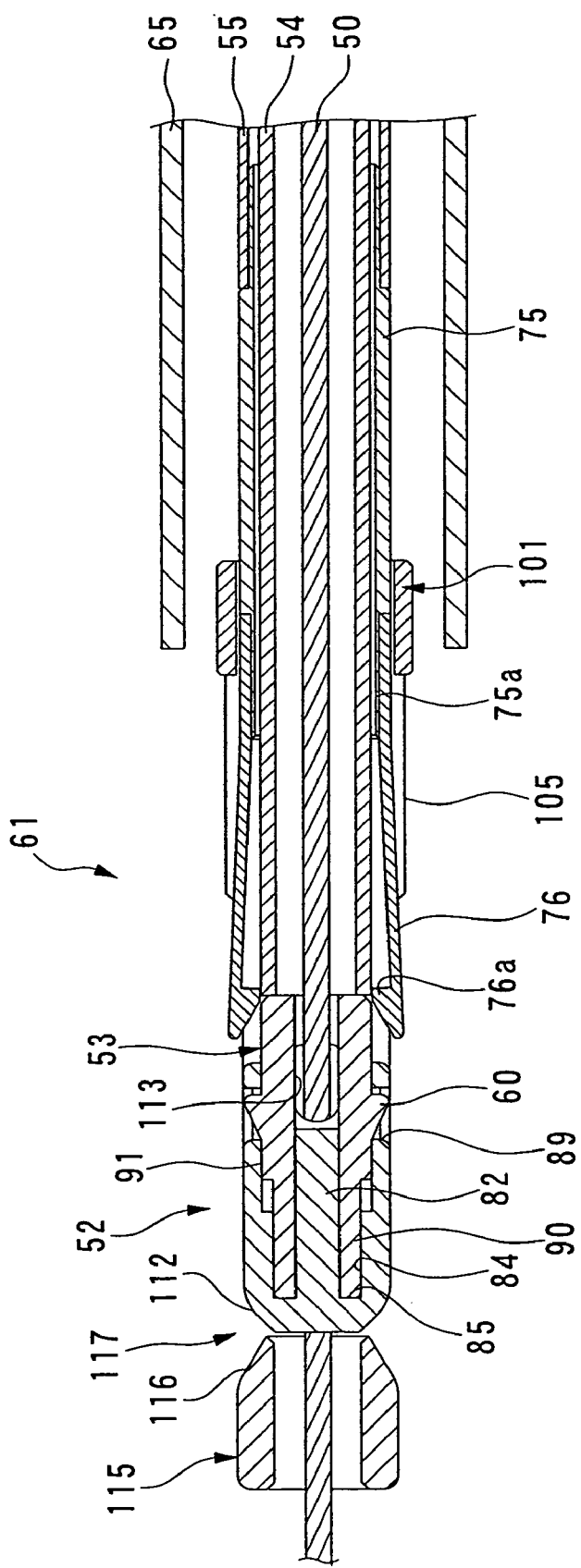
FIG. 33 is a cross-sectional view showing a condition where a cutting member is moved from the condition shown in FIG. 31, to cut the ligation wire.
Figure 34:
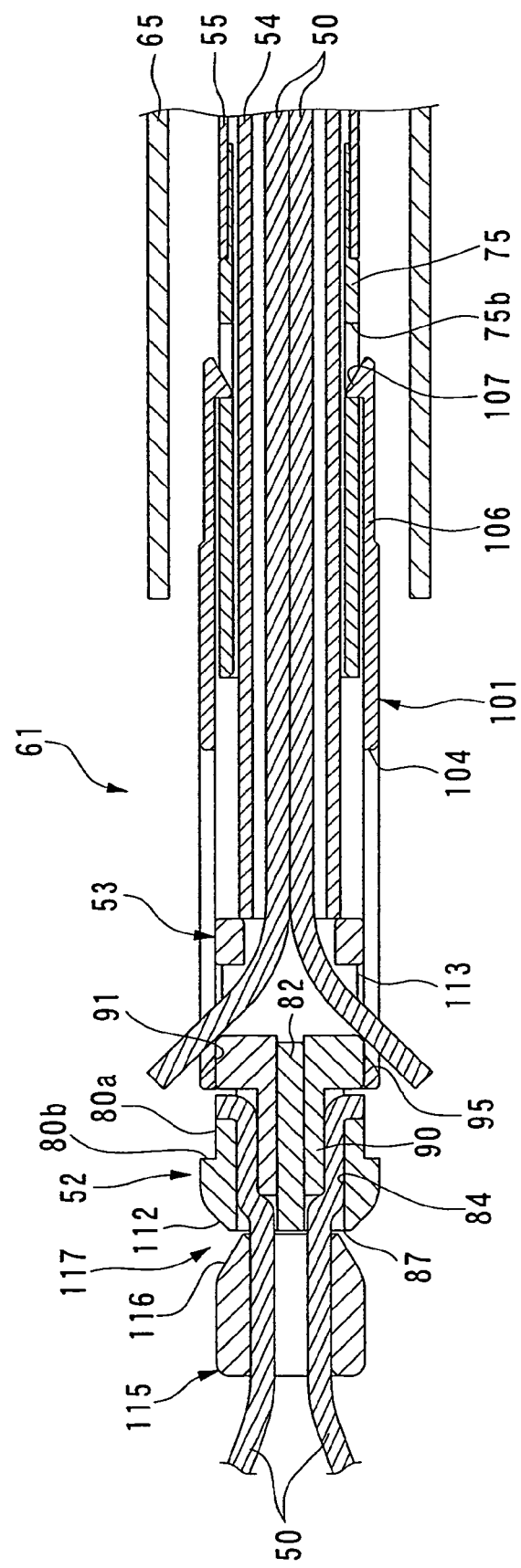
FIG. 34 is a cross-sectional view showing the ligation wire in the condition shown in FIG. 33.

After the connection between the linkage hooks 76 and the first member 52 is released, if the engagement grip 56 is pulled in the proximal direction, then as described above, since there is a small amount of play between the linkage holes 75b and the linkage catches 107, only the engagement sheath 55 is moved backward. Then, due to the further movement of the engagement sheath 55, the distal ends of the linkage holes 75b are abutted against the linkage catches 107, and the cutting member 101 is move in the proximal direction together with the engagement sheath 55. Then, as shown in FIG. 33 and FIG. 34, the cutting blades 95 are moved from the arm receivers 80a of the first member 52 toward the ligation wire 50, and cut the ligation wire 50.

At this time, the ligation wire 50 is cut so as to be exposed from the arm receivers 80a to the outside.

The doctor watches the endoscopic image displayed on the monitor 39, for example the latched condition of the first member 52 and the second member 53 and the movement of the cutting member 101, to confirm that the ligation wire 50 is reliably held and cut. Then he operates the endoscope so as to slowly separate the distal end of the insertion portion 63 from the affected part. At this time, the cutting member 101 is also taken out from the first member 52 and the second member 53. As a result, the ligation wire 50 held in the tightly bound condition by the first member 52 and the second member 53, is anchored in the body. As a result, the tight binding treatment of the affected part is completed.

At the time of the abovementioned cutting of the ligation wire 50, in the condition where the inner sheath 54 is pushed so as to push the tubular member 115 against the affected part and the operation wire 66 is pulled, the engagement sheath 55 is pulled to the hand side to latch the first member 52 and the second member 53. As a result, the ligation wire 50 can be held and fixed therebetween while ligating the affected part more reliably.

Figure 35:
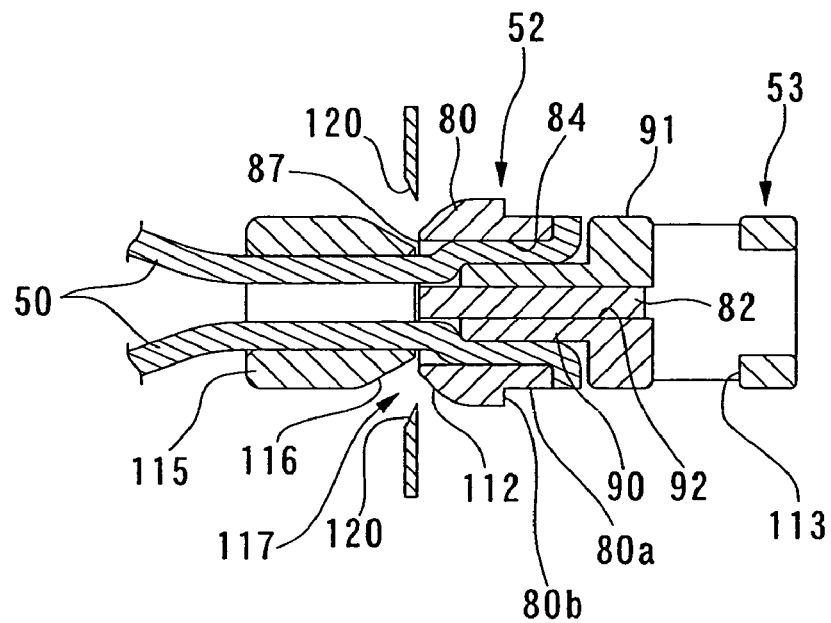
FIG. 35 is a cross-sectional view showing a state where a ligation wire is cut by clamp forceps, as a pretreatment before re-performing the ligation, after the biological tissue is ligated.

Here, supposing that the ligation of the affected part is loose, it is possible to ligate the affected part again, by cutting the ligation wire 50 so as to release the ligation of the affected part. That is, after the medical treatment tool 100 is taken out from the treatment tool channel 4, the doctor inserts publicly-known clamp forceps having, for example, a pair of cutting blades 120 as shown in FIG. 35. While watching the endoscopic image on the monitor 39, he inserts the cutting blades 120 in from the annular concavity 117, and cuts the ligation wire 50 (in FIG. 35, only the cutting blades 120 of the clamp forceps are shown for better understanding). At this time, the cutting blades 120 are guided between the first member 52 and the tubular member 115, by the annular concavity 117. Consequently, the doctor can readily operate the clamp forceps while merely watching the monitor 39, so as to cut the ligation wire 50.

As described above, according to the medical treatment tool 100 of the present embodiment, the first member 52 is moved toward the second member 53 without involving the affected part, so that the ligation wire 50 can be held and fixed between both members 52 and 53. Moreover, after the ligation wire 50 is fixed, the ligation wire 50 can be cut rearward of the holding position, by the cutting member 101. In this manner, since the ligation wire 50 is held and fixed before the ligation wire 50 is cut, the biological tissue can be more reliably ligated. Consequently, the reliability of the ligation operation can be improved.

Moreover, since the ligation wire 50 can be held, fixed, and cut, by a series of operations of the engagement grip 56, effective ligation operation can be performed without taking time. In particular, since the holding and fixing of the ligation wire 50 is not performed at the same time as the cutting thereof, then the engagement grip 56 can be readily operated without much force, and the operability can be improved.

Furthermore, since the ligation wire 50 is cut so as not to expose the cut ends to the outside of the arm receivers 80a of the first member 52, interference with other treatment tools such as the abovementioned clamp forceps or the endoscope insertion portion 10 can be prevented.

Moreover, since the cutting member 101 is detachably provided on the engagement sheath 55, it can be changed at each time of cutting. Consequently, the cutting blades 95 are always in a new condition, and their sharpness does not decrease.

Next, hereunder is a description of a third embodiment of a medical treatment tool according to the present invention, with reference to FIG. 36 to FIG. 40. In this third embodiment, the same reference symbols are used for components the same as those in the second embodiment, and description thereof is omitted.

The point where the third embodiment is different to the second embodiment is that in the medical treatment tool 100 of the second embodiment, the cutting blades 95 are provided on the distal edges of the wire slits 104, so as to cut the ligation wire 50 right after being guided from the slits 111 of the first member 52 to the outside, whereas in the medical treatment tool 130 of the third embodiment, the cutting blades 95 are arranged so as to cut the ligation wire 50 right before being guided from the side holes 113 of the second member 53 into the second member 53.

That is, as shown in FIG. 36 to FIG. 39, regarding the cutting member 101 of the medical treatment tool 130 of the present embodiment, in the center of the peripheral face of the distal arm 102 is formed a distal wire slit 131 from the distal end to the proximal side in the axial direction. Moreover, on the proximal side of the distal wire slit 131 is formed a hand-side wire slit 132. Furthermore, the cutting blade 95 is formed on the distal edge of the hand-side wire slit 132.

Figure 37:
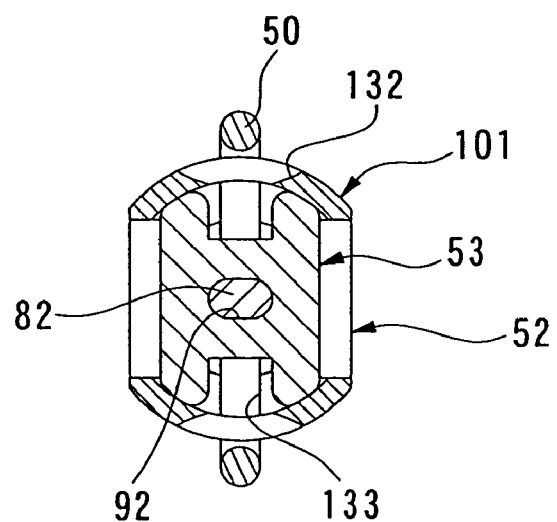
FIG. 37 is a cross-sectional view of the medical treatment tool shown in FIG. 36 taken along the line L-L.

Moreover, the second member 53 of the present embodiment is provided with wire grooves (wire storage portions) 133 which contain the cut ends of the cut ligation wire 50 therein. That is, as shown in FIG. 36 and FIG. 37, the distal side of the large diameter portion 91 is formed with a pair of the wire grooves 133 for guiding the ligation wire 50 that has been guided from the slits 111 of the first member 52 to the outside of the first member 52, into the second member 53.

As described above, the ligation wire 50 of the present embodiment is passed from the fixing hollow 84 of the first member 52, through the slits 111 and the distal wire slits 131 of the cutting member 101, then briefly comes out to the outside of the cutting member 101, and then is guided through the hand-side wire slits 132 of the cutting member 101 and the wire grooves 133 of the second member 53, into the second member 53. Moreover, the ligation wire 50 guided into the second member 53 is inserted into the inner sheath 54 to be coupled with the coupling member 66a via the folded portion 50b.

Figure 36:
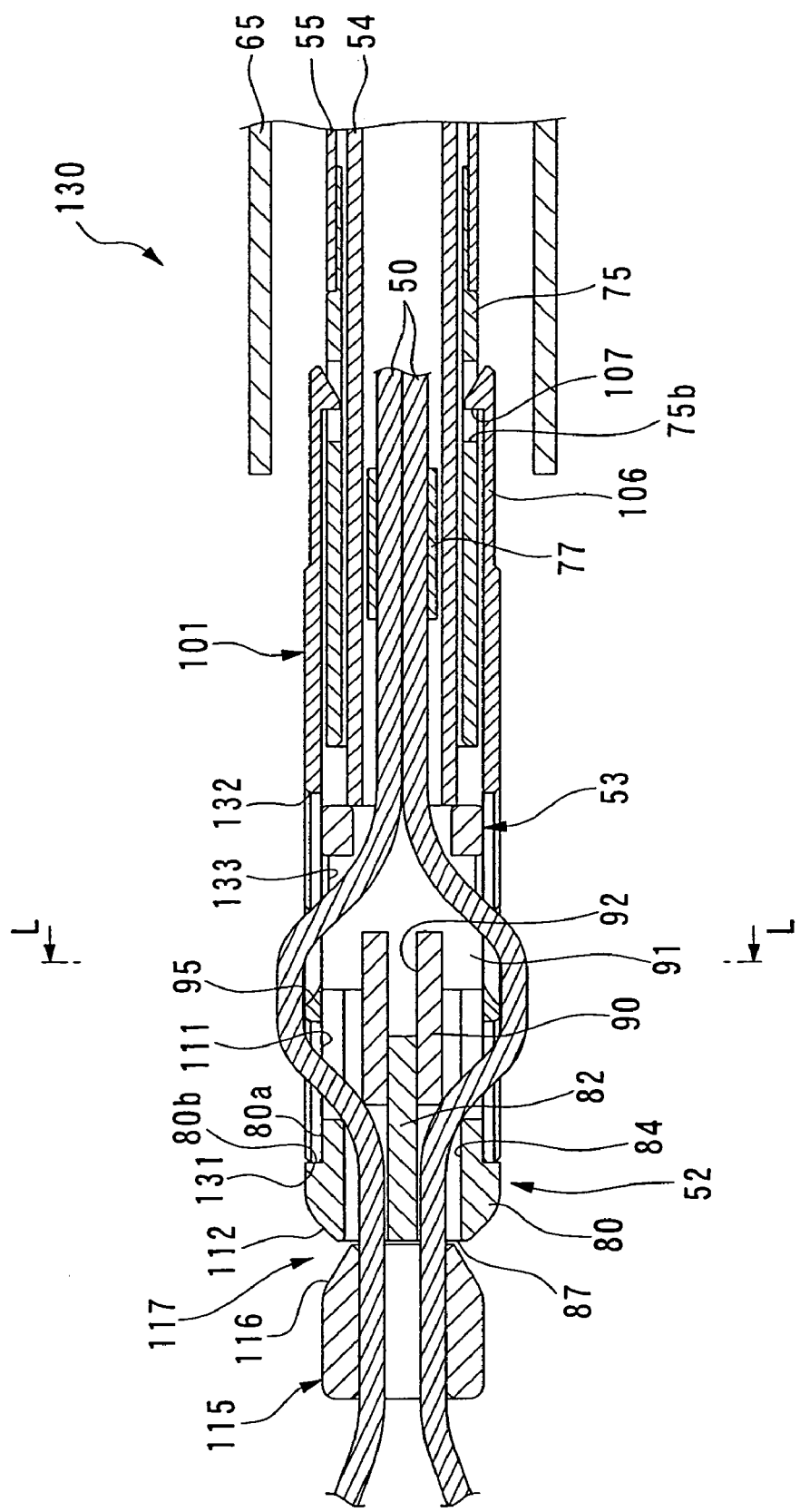
FIG. 36 is a cross-sectional view in the vicinity of the medical ligation tool showing a third embodiment of the medical treatment tool of the present invention.
Figure 38:
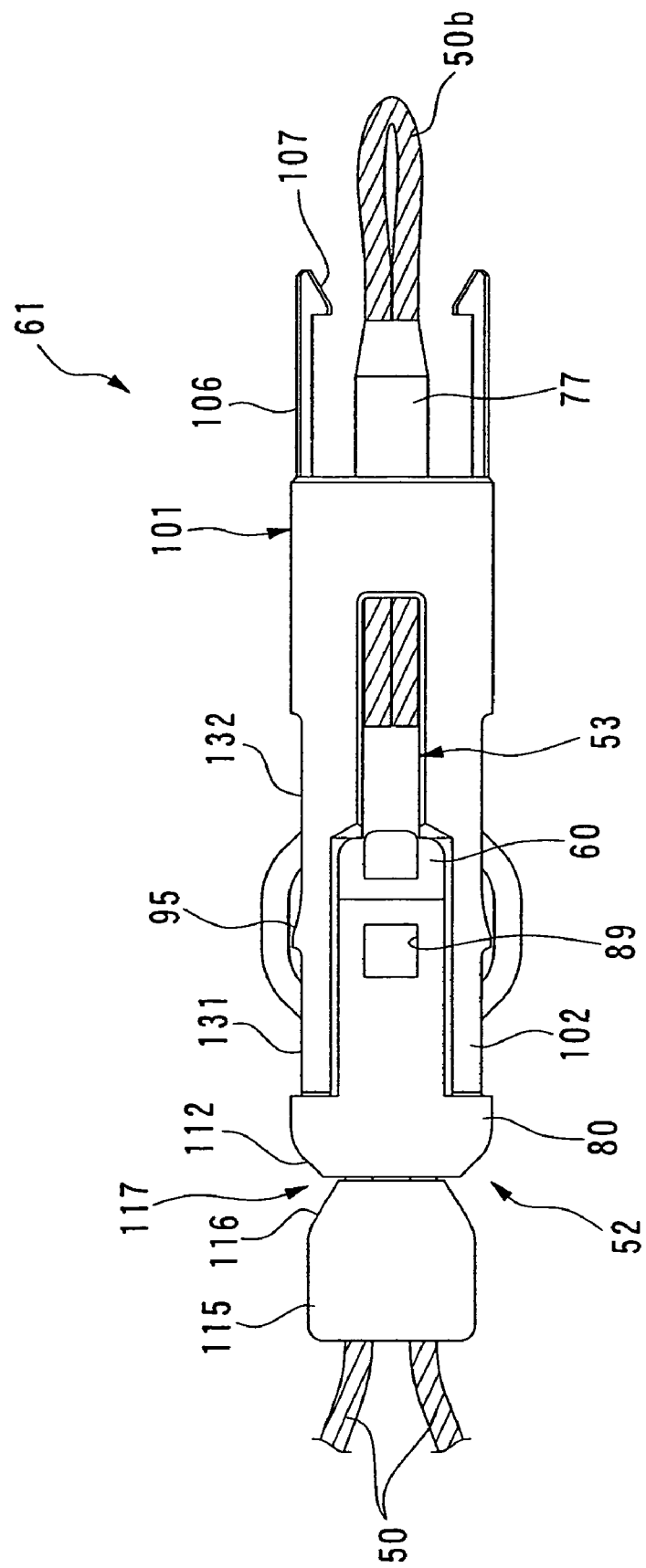
FIG. 38 is a top view of the medical ligation tool of the medical treatment tool shown in FIG. 36.
Figure 39:
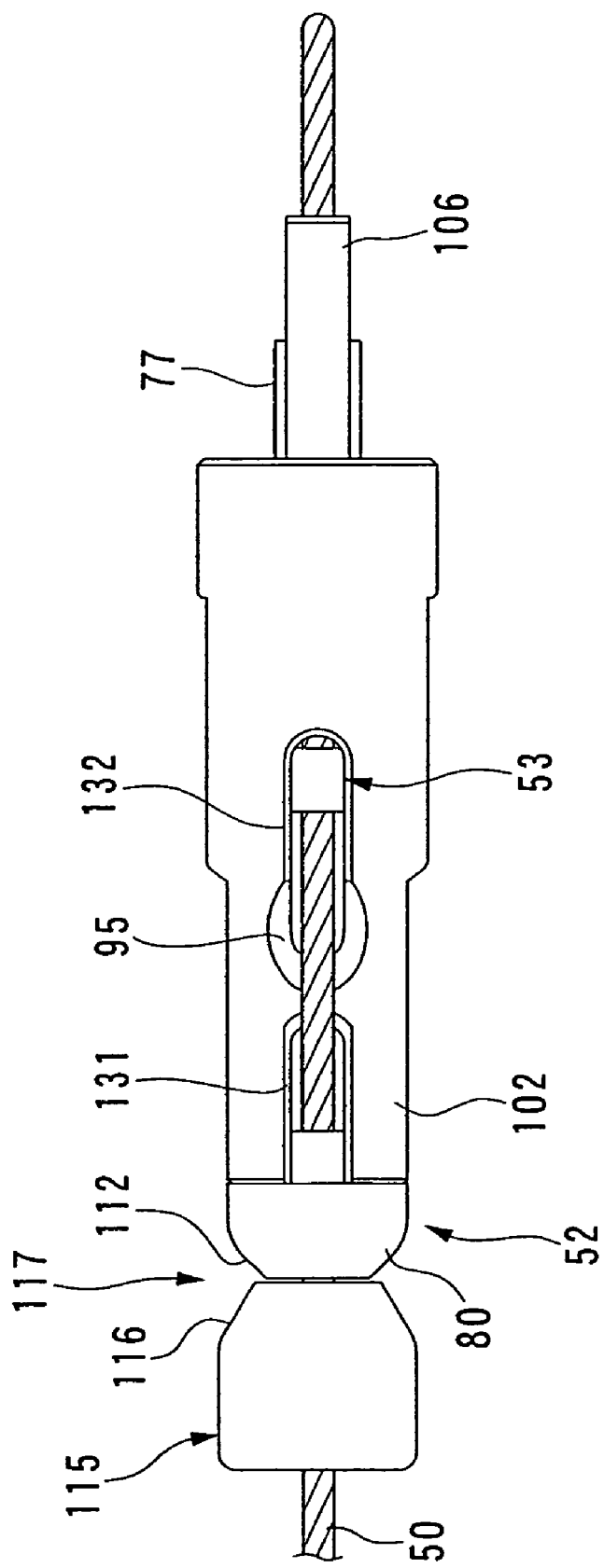
FIG. 39 is a side view of the medical ligation tool of the medical treatment tool shown in FIG. 36.

In the medical treatment tool 130 constituted in this manner, as shown in FIG. 36, when cutting the ligation wire 50, the cutting blades 95 cut the ligation wire 50 that has been guided from the outside of the cutting member 101 into the second member 53. Since this ligation wire 50 to be cut is in a condition where it is difficult to be moved in the proximal direction, the cutting blades 95 reliably come up against the ligation wire 50. That is, the cutting blades 95 come up against the ligation wire 50 at an angle where they are unlikely to slide. Consequently, the ligation wire 50 can be more readily cut, and the operability of the ligation treatment can be improved.

Figure 40:
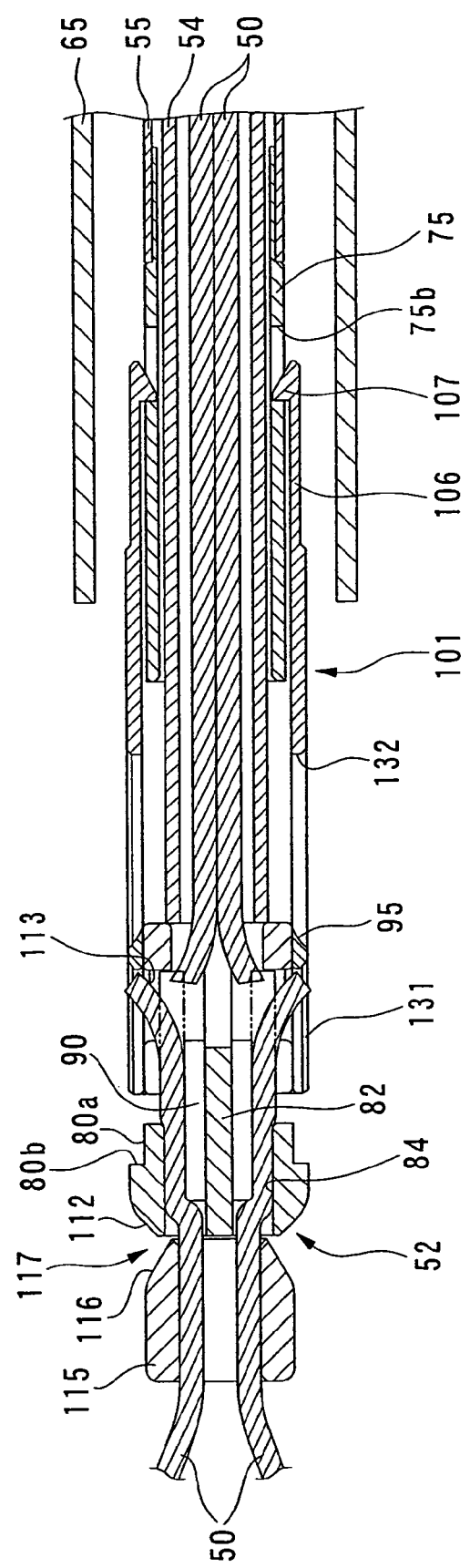
FIG. 40 is a cross-sectional view showing a condition where the ligation wire is cut by the medical treatment tool shown in FIG. 36, after the biological tissue is ligated.

Moreover, as shown in FIG. 40, the cut ends of the cut ligation wire 50 are contained in the wire grooves 133 of the second member 53. Consequently, after being cut, the cut ends of the ligation wire 50 are not exposed to the outside of the second member 53, and interference with other treatment tools or the endoscope insertion portion 10 can be prevented.

Next, hereunder is a description of a fourth embodiment of a medical treatment tool according to the present invention, with reference to FIG. 41 to FIG. 46. In this fourth embodiment, the same reference symbols are used for components the same as those in the first embodiment, and description thereof is omitted.

The point where the fourth embodiment is different to the first embodiment is that in the first embodiment, the medical treatment tool serves as the ligation unit which ligates an affected part of the biological tissue, and the wire serves as the ligation wire 50, whereas in the medical treatment tool 140 of the fourth embodiment, the medical treatment tool serves as a suture unit which sutures an affected part that is bleeding or the like, and the wire serves as a suture thread 141.

Figure 41:
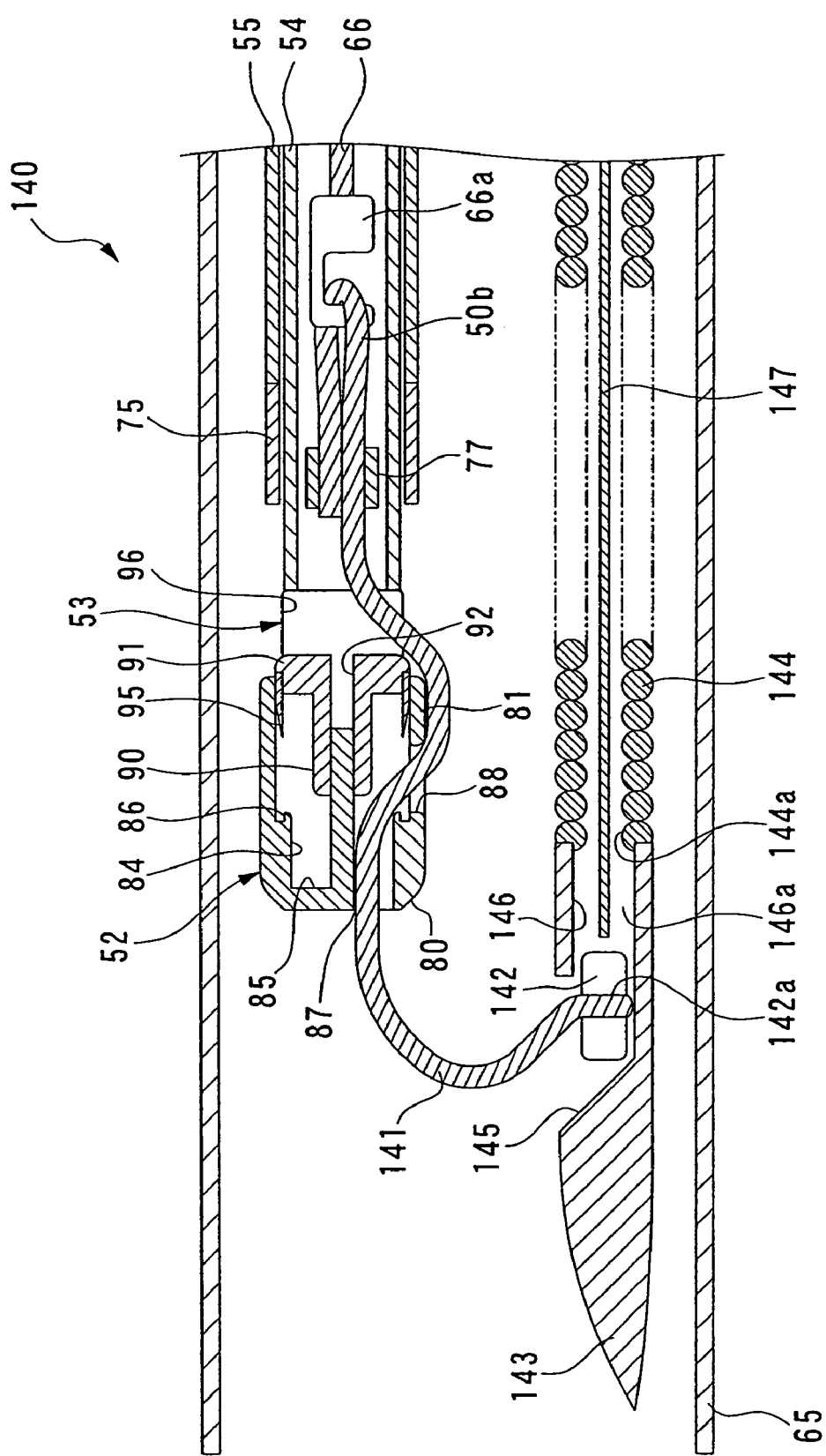
FIG. 41 is a cross-sectional view of a distal end of an insertion portion, showing a fourth embodiment of the medical treatment tool of the present invention.

That is, as shown in FIG. 41, the medical treatment tool 140 of the present embodiment comprises; a drop-off preventing tip (drop-off preventing member) 142 connected to the distal end of the suture thread 141, and a suture needle main body 144 which detachably contains the drop-off preventing tip 142, and has a needle portion 143 for piercing the biological tissue, on the distal end.

The suture needle main body 144 is formed in a pipe shape by a closely wound coil, and is flexible so as to be curved in the treatment tool channel 4. Moreover, the distal end of the suture needle main body 144 is attached with the needle portion 143. The needle portion 143 is formed from a metallic member such as stainless steel, so that the distal end is formed in a sharp slender shape, and the outer diameter is the same as that of the suture needle main body 144. Moreover, on the side face of the needle portion 143 is formed an opening 145. This opening 145 is formed with a storage portion 146 communicated with an inner hole 144a of the suture needle main body 144, so that the drop-off preventing tip 142 can be contained therein.

The drop-off preventing tip 142 is formed in a column shape, and the distal end of the suture thread 141 is bound around an intermediate indentation 142a. The drop-off preventing tip 142 is contained in the storage portion 146, having the axial direction matched with the axial direction of the suture needle main body 144. Moreover, in the storage portion 146 is formed an engagement hole 146a engaged with the end of the drop-off preventing tip 142. By containing the drop-off preventing tip 142 so as to engage the end thereof into the engagement hole 146a, it does not easily drop off from the storage portion 146.

Moreover, a flexible push-out wire 147 for pushing out the drop-off preventing tip 142 that has been contained in the storage portion 146, from the storage portion 146, is arranged in the inner hole 144a of the suture needle main body 144, in a back-and-forth movable manner. The push-out wire 147 can be operated back-and-forth by the hand-side operation portion 64.

Furthermore, the suture thread 141 is passed from the drop-off preventing tip 142, through the first member 52 and the second member 53, and is coupled with the coupling member 66a.

Moreover, in the present embodiment, the outer sheath 65 is designed to cover the engagement sheath 55 and the suture needle main body 144. That is, the suture needle main body 144 is constructed so as to be back-and-forth movable separately from the engagement sheath 55, in the outer sheath 65. Furthermore, the suture needle main body 144 can be also operated by the hand-side operation portion 64.

Moreover, regarding the distal hole 87 and the side hole 88 of the first member 52, they are not formed in pair, but each one of them is individually formed.

Hereunder is a description of a case where the affected part is sutured by the medical treatment tool 140 constituted in such a manner.

Firstly, after the doctor judges by the endoscopic image displayed on the monitor 39, that the distal end of the endoscope insertion portion 10 has reached the affected part to be sutured, he positions the distal end of the endoscope insertion portion 10 in the vicinity of the affected part while watching the monitor 39. Next, in this condition, the doctor inserts the medical treatment tool 140 into the treatment tool channel 4 through the treatment tool through hole 15. At this time, the doctor moves the grip 72 in the distal direction and inserts the outer sheath 65 into the treatment tool channel 4, in a condition as shown in FIG. 41 where the outer sheath 65 is covered around the engagement sheath 55 and the suture needle main body 144.

Figure 42:
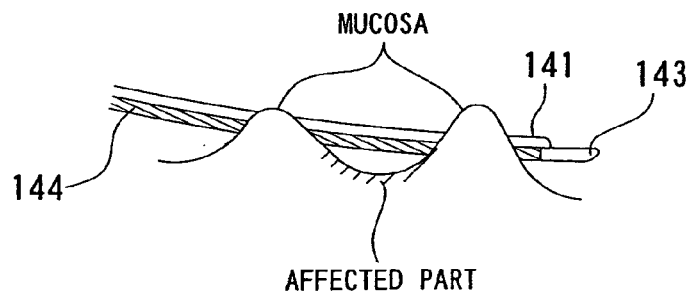
FIG. 42 shows a condition where mucosa around an affected part is pierced by a suture needle main body of the medical treatment tool shown in FIG. 41.

Then, after the doctor confirms by the endoscopic image displayed on the monitor 39, that the outer sheath 65 is projected from the distal face of the endoscope insertion portion 10, he moves the grip 72 in the proximal direction, so as to move the outer sheath 65 backward. Moreover, the doctor operates the suture needle main body 144 while watching the monitor 39, so as to, as shown in FIG. 42, pass the needle portion 143 through, by piercing the mucosa in front of the affected part to be stopped bleeding, and by piercing the mucosa on the opposite side with respect to the affected part, with the needle portion 143.

In this case, the suture thread 141 is sufficiently long so as not to limit the movement of the suture needle main body 144.

Figure 43:
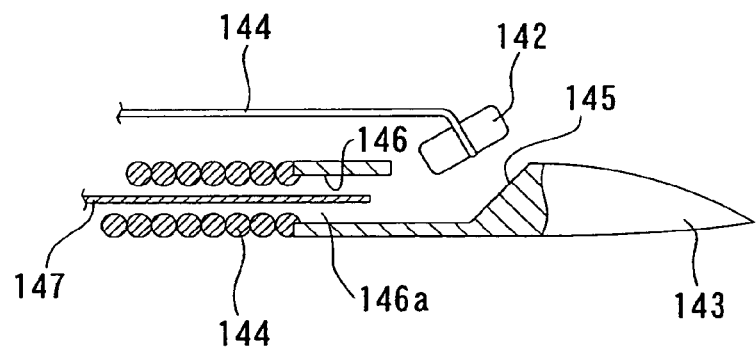
FIG. 43 is a side view of the suture needle main body, showing a condition where a drop-off preventing tip is detached from the suture needle main body of the medical treatment tool shown in FIG. 41.
Figure 44:
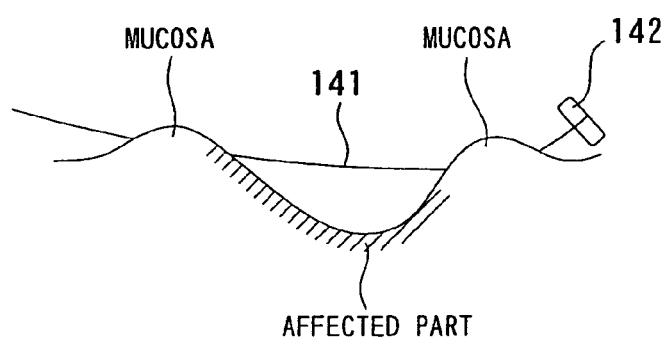
FIG. 44 shows a condition where the suture needle main body is withdrawn from the condition of FIG. 41.

In this condition, as shown in FIG. 43, the push-out wire 147 is pushed out in the distal direction, to take out the drop-off preventing tip 142 from the engagement hole 146a, and to push it out from the storage portion 146. As a result, the drop-off preventing tip 142 is detached from the suture needle main body 144. After the drop-off preventing tip 142 is detached, the suture needle main body 144 is withdrawn, so that as shown in FIG. 44, the drop-off preventing tip 142 is hooked on the biological tissue, and the suture thread 141 connected to the drop-off preventing tip 142 is passed through the opposite mucosa portions that have been pierced by the needle portion 143.

Figure 45:
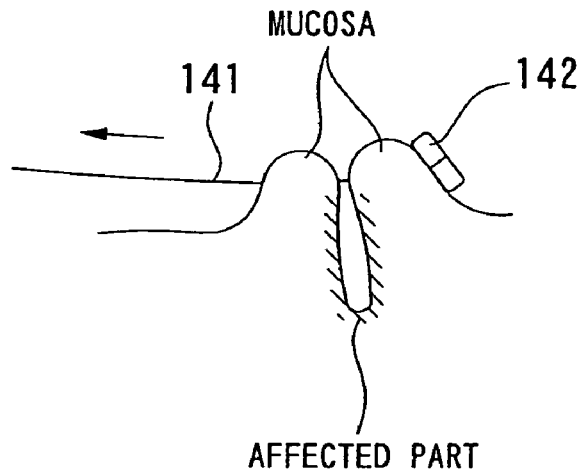
FIG. 45 shows a condition where a suture thread is pulled from the condition of FIG. 43, and the mucosa is superposed so as to close the affected part.
Figure 46:
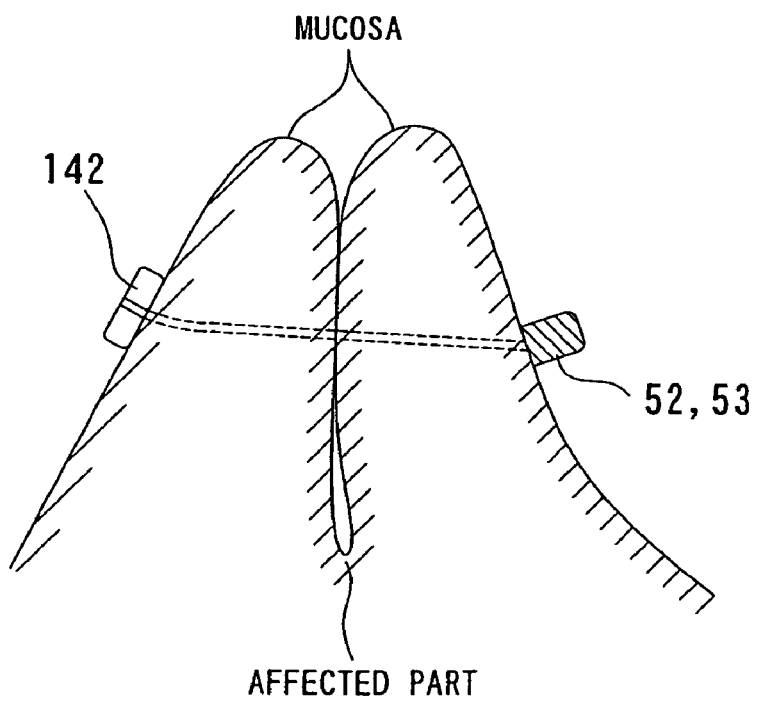
FIG. 46 shows a condition where the suture thread is fixed by a stopper from the condition of FIG. 45, to cut the suture thread.

Next, in this condition, the slider 71 is operated in the proximal direction, to pull the operation wire 66a, so that as shown in FIG. 45 the pierced mucosa portions are pulled together. That is, the suture thread 141 gathers the opposite pierced mucosa portions, to close the affected part being the bleeding part. Then, in the condition where the first member 52 is in contact with the mucosa portion, the affected part is closed. Then, the engagement grip 56 is moved in the proximal direction, so as to operate to pull the engagement sheath 55, so that the suture thread 141 can be reliably cut by means of the cutting blades 95, while being held between the first member 52 and the second member. After the suture thread 141 is cut, as shown in FIG. 46, the affected part is sutured in the closed condition, and reliably fixed by means of the first member 52 and the second member 53. As a result, the suture treatment of the affected part is completed.

The technical scope of the present invention is not limited to the above embodiments, and various modifications can be made without departing from the scope of the present invention.

In the respective embodiments, the latching device is constituted by the latch holes of the connection device and the coupling catches serving as the connection releasing device. However, it is not limited to this, and may be separately provided.

Moreover, in the second embodiment and the third embodiment, the connection member is detachably provided on the engagement sheath via the linkage pipe. However, it is not limited to the detachable type, and may be fixed on the distal end of the engagement sheath. Furthermore, in the third embodiment, the structure is such that the tubular member is provided on the distal side of the first member. However this structure is not limited only to the third embodiment, and may be applied to the other respective embodiments.

Moreover, there are shown examples where the medical treatment tool of the present embodiment is applied to the ligation unit and the suture unit, however it is not limited to these.

According to the medical treatment tool of the present invention, the first wire holding member is moved toward the second wire holding member without involving the biological tissue, so that the wire which has completed a predetermined treatment, can be held and fixed between both members, and can be cut rearward of the holding position. That is, since the wire can be reliably held, fixed, and cut, regardless of the condition of the biological tissue, the operability and the accuracy of the workability can be improved.

Moreover, since by a series of operations of the sheath operation portion at approximately the same time, the wire can be held, fixed, and cut, by latching the first wire holding member and the second wire holding member, and the connection of the first wire holding member and the second sheath can be released, effective operation can be performed.

INDUSTRIAL APPLICABILITY

The present invention can be used as a medical treatment tool which is inserted into a body cavity, so as to perform a predetermined treatment, such as ligation and suture, on a biological tissue.

According to the present invention, after the predetermined treatment on the biological tissue, a wire such as a ligation wire can be fixed and cut without involving the biological tissue.

The invention claimed is:
1. A medical treatment tool, comprising:
a flexible wire configured to perform a predetermined treatment on a biological tissue;
a wire operation portion which is configured to operate said wire back-and-forth;
a first wire holding member which is provided in a back-and-forth movable manner with respect to said wire, to hold the wire;
a second wire holding member which is provided on a proximal side of said first wire holding member, in a back-and-forth movable manner in an axial direction, and is capable of holding said wire between itself and the first wire holding member;
a flexible first sheath which is provided in contact with a proximal side of said second wire holding member;
a flexible second sheath which is provided to cover said first sheath, in a back and-forth movable manner with respect to the first sheath; and
a sheath operation portion which operates said second sheath back-and-forth;
wherein said first wire holding member and said second sheath have a connection device which connects them to each other; and
a connection releasing device which is configured to cause said second wire holding member to engage with said first wire holding member to limit the motion of said flexible wire to said first wire holding member, and which is configured to reset the connection between said first wire holding member and said second sheath thereby releasing said first wire holding member and said second wire holding member from said first sheath and said second sheath, respectively wherein the connection device comprises a pair of flexible projecting members which are deformable in a radial direction of the second sheath and projected from a proximal end to a distal end along an extension line of a periphery of the second sheath and each having a catch element jutted out inwardly on the distal end and a pair of latch holes each of which is perforated through the side wall of the first wire holding member and being deformable in the radial direction of the second sheath with which latch holes the catch elements are engaged respectively to the inside the first wire holding member to thereby connect the first wire holding member with the second sheath and wherein the first wire holding member and the second wire holding member have a latching device for latching with each other upon holding the wire therebetween, comprising the first coupling catch elements and the latch holes, and the connection releasing device comprising a coupling catch disposed to a position corresponding to the latch holes, on the second wire holding member, the connection releasing device having a wedge-like shape element expanding from the side wall surface at the distal end side of the second wire holding member to a top portion and having an external diameter slightly larger than an external diameter of the first wire holding member, disposed on the proximal end side thereof, wherein when the second wire holding member moves forwardly to the first wire holding member; said coupling catch is engaged into the latch hole on the second wire holding member, thereby releasing the connection between the first wire holding member and the second sheath to thereby connect the first wire holding member and the second wire holding member.

2. The medical treatment tool as set forth in claim 1, wherein at least one of the first wire holding member and the second wire holding member have a cutting member comprising a cutting device configured for cutting the wire at the proximal side of the holding portion, and
wherein the second wire holding member moves forwardly to the first wire holding member, so as to make the second wire holding member be engaged with the first wire holding member, thereby releasing the connection between the first wire holding member and the second sheath to connect the first wire holding member and the second wire holding member and to cut the flexible wire and hold the cut flexible wire by catching the wire between the first wire holding member and the second wire holding member.

3. A medical treatment tool according to claim 2, wherein said cutting member is detachably provided on said second sheath.

4. A medical treatment tool according to claim 1, wherein said wire is a ligation wire which ligates a biological tissue.

5. A medical treatment tool according to claim 1, wherein said wire is a suture thread for suturing a biological tissue, and there is provided;
a drop-off preventing member connected to a distal end of said suture thread; and a suture needle main body which detachably contains said drop-off preventing member, and has a needle portion for piercing a biological tissue, on a distal end.

6. A medical treatment tool according to claim 2, wherein said wire is a ligation wire which ligates a biological tissue.

7. A medical treatment tool according to claim 2, wherein said wire is a suture thread for suturing a biological tissue, and there is provided;
- a drop-off preventing member connected to a distal end of said suture thread; and
- a suture needle main body which detachably contains said drop-off preventing member, and has a needle portion for piercing a biological tissue, on a distal end.

8. A medical treatment tool according to claim 2, wherein said second wire holding member has a wire storage portion which contains a cut end of said wire after cutting, thereinside.

9. The medical treatment tool as set forth in claim 1, wherein at least one of the first wire holding member and the second wire holding member have a cutting member comprising a cutting device configured for cutting the wire at the proximal side of the holding portion, and
- wherein the second wire holding member moves forwardly to the first wire holding member, said coupling catch is configured to be engaged into the latch hole, thereby releasing the connection between the first wire holding member and the second sheath to connect the first wire holding member with the second wire holding member and to cut the flexible wire and hold the cut flexible wire by catching the wire between the first wire holding member and the second wire holding member.

* * * * *